(12) United States Patent
Fetissov et al.

(10) Patent No.: US 11,369,645 B2
(45) Date of Patent: Jun. 28, 2022

(54) HAFNIA ALVEI IMPACT ON REGULATION OF APPETITE AND METABOLIC SYNDROME ASPECTS

(71) Applicants: Institut National de la Sante et de la Recherche Medicale (INSERM), Paris (FR); Centre Hospitalier Universitaire de Rouen, Rouen (FR); Universite de Rouen, Mont-Saint Aignan (FR); TARGEDYS, Rouen (FR)

(72) Inventors: Serguei Fetissov, Rouen (FR); Pierre Dechelotte, Rouen (FR); Jonathan Breton, Rouen (FR); Gregory Lambert, Châtenay-Malabry (FR); Nicolas Lucas, Rouen (FR); Romain Legrand, Rouen (FR)

(73) Assignees: INSTITUT NATIONAL DE LA SANTE ET DE LA RECHERCHE MEDICALE (INSERM), Paris (FR); CENTRE HOSPITALIER UNIVERSITAIRE DE ROUEN, Rouen (FR); UNIVERSITE DE ROUEN, Mont-Saint Aignan (FR); TARGEDYS, Rouen (FR)

( * ) Notice: Subject to any disclaimer, the term of this patent is extended or adjusted under 35 U.S.C. 154(b) by 0 days.

(21) Appl. No.: 16/902,732

(22) Filed: Jun. 16, 2020

(65) Prior Publication Data

US 2021/0008125 A1   Jan. 14, 2021

Related U.S. Application Data

(63) Continuation-in-part of application No. 16/032,604, filed on Jul. 11, 2018, now Pat. No. 10,729,770, (Continued)

(30) Foreign Application Priority Data

Dec. 5, 2013   (EP) ..................................... 13306673
Oct. 2, 2014   (EP) ..................................... 14306552
May 6, 2015   (WO) .................. PCT/IB2015/001126

(51) Int. Cl.
*A61K 35/741*   (2015.01)
*A61P 3/04*   (2006.01)
(Continued)

(52) U.S. Cl.
CPC .......... *A61K 35/741* (2013.01); *A23L 33/135* (2016.08); *A61P 3/04* (2018.01);
(Continued)

(58) Field of Classification Search
CPC ........ A23V 2002/00; A23V 2200/3204; A23V 2200/332; A61P 3/04; A61P 3/10;
(Continued)

(56) References Cited

PUBLICATIONS

Legrand et al. "Commensal Hafnia alvei strain reduces food intake and fat mass in obese mice—a new potential probiotic for appetite and body weight management", International Journal of Obesity, 2020-01.

(Continued)

*Primary Examiner* — Jana A Hines
(74) *Attorney, Agent, or Firm* — WCF IP

(57) ABSTRACT

The present invention relates to method of preventing, treating or attenuating obesity-related manifestations in a human or non-human mammal subject in need thereof, said method comprising orally administering to the subject a composition comprising an effective amount *Hafnia alvei* probiotics; wherein said obesity-related parameters are selected from the group of hyperphagia, increased fat mass
(Continued)

Figure 2A:
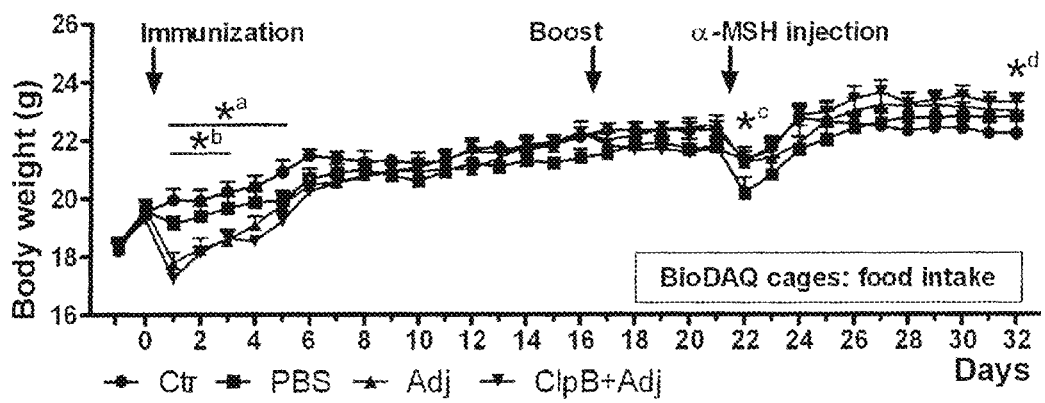

on lean mass ratio, increased waist circumference, postprandial hyperglycemia, fasting hyperglycemia and hypercholesterolemia.

8 Claims, 21 Drawing Sheets

Specification includes a Sequence Listing.

Related U.S. Application Data which is a continuation-in-part of application No. 15/101,452, filed as application No. PCT/EP2014/076611 on Dec. 4, 2014, now abandoned, application No. 16/902,732, which is a continuation-in-part of application No. 15/579,459, filed as application No. PCT/IB2016/051923 on Apr. 5, 2016, now Pat. No. 10,682,389, application No. 16/902,732, which is a continuation-in-part of application No. 16/091,678, filed as application No. PCT/EP2017/058116 on Apr. 5, 2017, now Pat. No. 10,888,592.

(51) Int. Cl.
  *A61P 3/10* (2006.01)
  *A23L 33/135* (2016.01)
  *A61P 3/06* (2006.01)
  *A61K 35/00* (2006.01)

(52) U.S. Cl.
  CPC ............... *A61P 3/06* (2018.01); *A61P 3/10* (2018.01); *A23V 2002/00* (2013.01); *A61K 2035/115* (2013.01)

(58) Field of Classification Search
  CPC ... A61P 3/06; A61K 2035/115; A61K 35/741; A23L 33/135
  See application file for complete search history.

(56) References Cited

PUBLICATIONS

Lucas et al. "Hafnia alvei HA4597 Strain Reduces Food Intake and Body Weight Gain and Improves Body Composition, Glucose, and Lipid Metabolism in a Mouse Model of Hyperphagic Obesity" Microorganisms, 2020, 8:35.

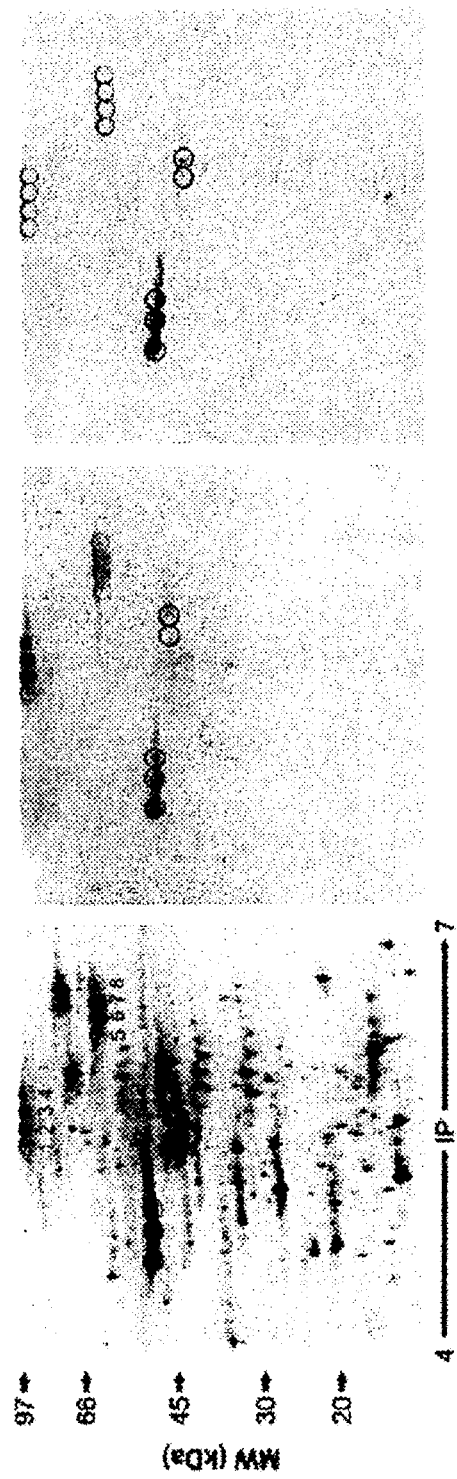

☐ before adsorption
■ adsorption with α-MSH $10^{-6}$M

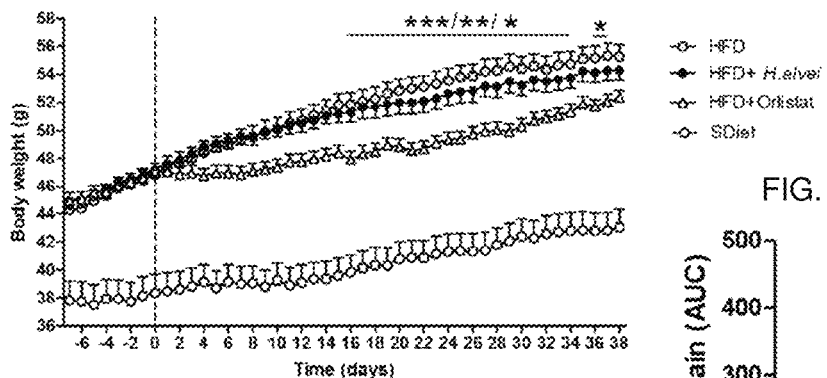
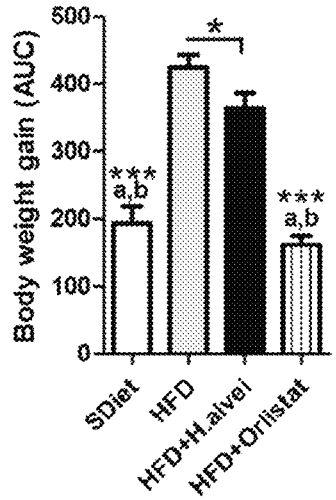
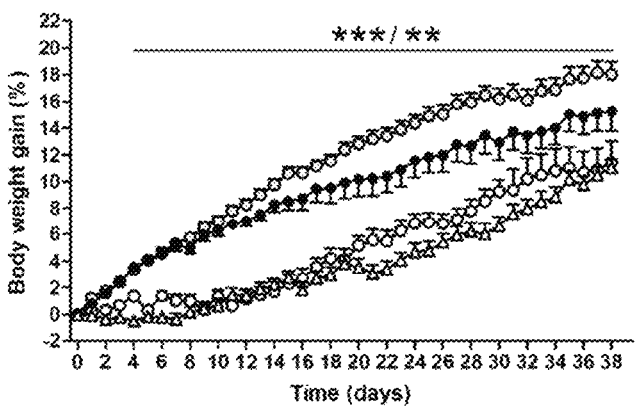
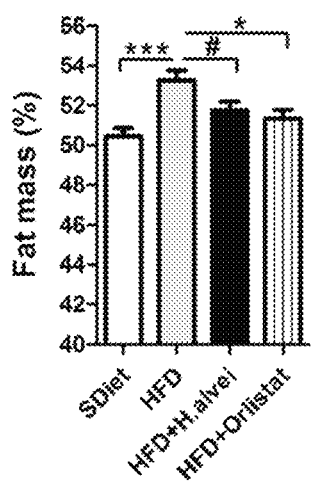
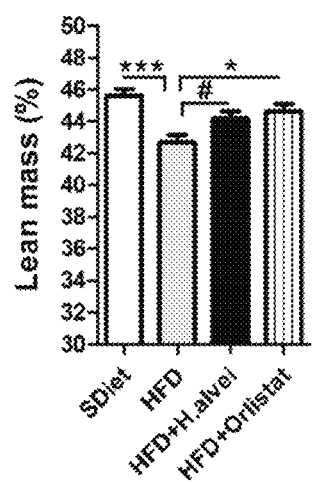
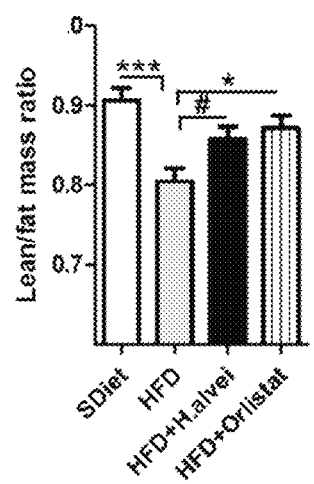

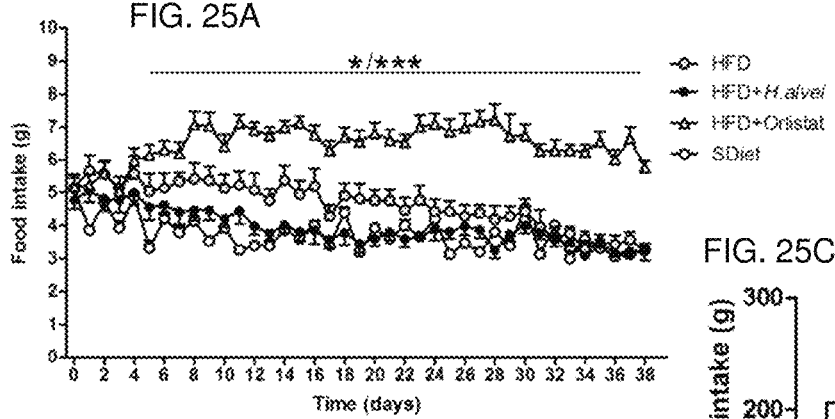
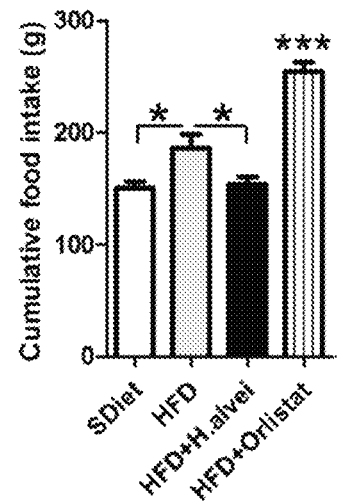
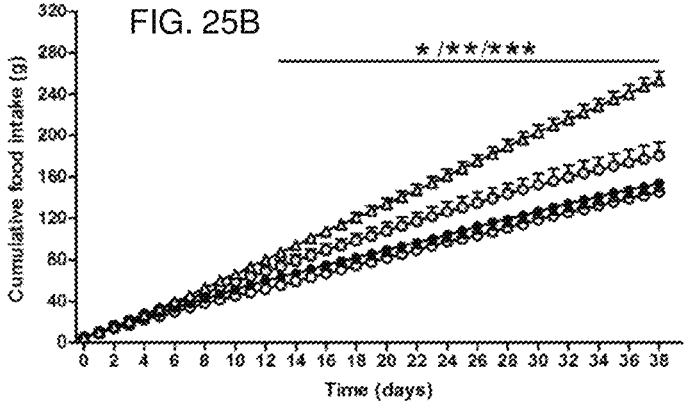

SEQUENCE LISTING

```
<160> NUMBER OF SEQ ID NOS: 5

<210> SEQ ID NO 1
<211> LENGTH: 857
<212> TYPE: PRT
<213> ORGANISM: Escherichia coli

<400> SEQUENCE: 1

Met Arg Leu Asp Arg Leu Thr Asn Lys Phe Gln Leu Ala Leu Ala Asp
1               5                   10                  15

Ala Gln Ser Leu Ala Leu Gly His Asp Asn Gln Phe Ile Glu Pro Leu
            20                  25                  30

His Leu Met Ser Ala Leu Leu Asn Gln Glu Gly Gly Ser Val Ser Pro
        35                  40                  45

Leu Leu Thr Ser Ala Gly Ile Asn Ala Gly Gln Leu Arg Thr Asp Ile
    50                  55                  60

Asn Gln Ala Leu Asn Arg Leu Pro Gln Val Glu Gly Thr Gly Gly Asp
65                  70                  75                  80

Val Gln Pro Ser Gln Asp Leu Val Arg Val Leu Asn Leu Cys Asp Lys
                85                  90                  95

Leu Ala Gln Lys Arg Gly Asp Asn Phe Ile Ser Ser Glu Leu Phe Val
            100                 105                 110

Leu Ala Ala Leu Glu Ser Arg Gly Thr Leu Ala Asp Ile Leu Lys Ala
        115                 120                 125

Ala Gly Ala Thr Thr Ala Asn Ile Thr Gln Ala Ile Glu Gln Met Arg
```

```
                130             135             140
Gly Gly Glu Ser Val Asn Asp Gln Gly Ala Glu Asp Gln Arg Gln Ala
145                 150                 155                 160

Leu Lys Lys Tyr Thr Ile Asp Leu Thr Glu Arg Ala Glu Gln Gly Lys
                165                 170                 175

Leu Asp Pro Val Ile Gly Arg Asp Glu Glu Ile Arg Arg Thr Ile Gln
                180                 185                 190

Val Leu Gln Arg Arg Thr Lys Asn Asn Pro Val Leu Ile Gly Glu Pro
                195                 200                 205

Gly Val Gly Lys Thr Ala Ile Val Glu Gly Leu Ala Gln Arg Ile Ile
                210                 215                 220

Asn Gly Glu Val Pro Glu Gly Leu Lys Gly Arg Arg Val Leu Ala Leu
225                 230                 235                 240

Asp Met Gly Ala Leu Val Ala Gly Ala Lys Tyr Arg Gly Glu Phe Glu
                245                 250                 255

Glu Arg Leu Lys Gly Val Leu Asn Asp Leu Ala Lys Gln Glu Gly Asn
                260                 265                 270

Val Ile Leu Phe Ile Asp Glu Leu His Thr Met Val Gly Ala Gly Lys
                275                 280                 285

Ala Asp Gly Ala Met Asp Ala Gly Asn Met Leu Lys Pro Ala Leu Ala
                290                 295                 300

Arg Gly Glu Leu His Cys Val Gly Ala Thr Thr Leu Asp Glu Tyr Arg
305                 310                 315                 320

Gln Tyr Ile Glu Lys Asp Ala Ala Leu Glu Arg Arg Phe Gln Lys Val
                325                 330                 335

Phe Val Ala Glu Pro Ser Val Glu Asp Thr Ile Ala Ile Leu Arg Gly
                340                 345                 350

Leu Lys Glu Arg Tyr Glu Leu His His His Val Gln Ile Thr Asp Pro
                355                 360                 365

Ala Ile Val Ala Ala Thr Leu Ser His Arg Tyr Ile Ala Asp Arg
                370                 375                 380

Gln Leu Pro Asp Lys Ala Ile Asp Leu Ile Asp Glu Ala Ala Ser Ser
385                 390                 395                 400

Ile Arg Met Gln Ile Asp Ser Lys Pro Glu Glu Leu Asp Arg Leu Asp
                405                 410                 415

Arg Arg Ile Ile Gln Leu Lys Leu Glu Gln Gln Ala Leu Met Lys Glu
                420                 425                 430

Ser Asp Glu Ala Ser Lys Lys Arg Leu Asp Met Leu Asn Glu Glu Leu
                435                 440                 445

Ser Asp Lys Glu Arg Gln Tyr Ser Glu Leu Glu Glu Glu Trp Lys Ala
450                 455                 460

Glu Lys Ala Ser Leu Ser Gly Thr Gln Thr Ile Lys Ala Glu Leu Glu
465                 470                 475                 480

Gln Ala Lys Ile Ala Ile Glu Gln Ala Arg Arg Val Gly Asp Leu Ala
                485                 490                 495

Arg Met Ser Glu Leu Gln Tyr Gly Lys Ile Pro Glu Leu Glu Lys Gln
                500                 505                 510

Leu Glu Ala Ala Thr Gln Leu Glu Gly Lys Thr Met Arg Leu Leu Arg
                515                 520                 525

Asn Lys Val Thr Asp Ala Glu Ile Ala Glu Val Leu Ala Arg Trp Thr
                530                 535                 540

Gly Ile Pro Val Ser Arg Met Met Glu Ser Glu Arg Glu Lys Leu Leu
545                 550                 555                 560
```

-continued

```
Arg Met Glu Gln Glu Leu His His Arg Val Ile Gly Gln Asn Glu Ala
                565                 570                 575
Val Asp Ala Val Ser Asn Ala Ile Arg Arg Ser Arg Ala Gly Leu Ala
            580                 585                 590
Asp Pro Asn Arg Pro Ile Gly Ser Phe Leu Phe Leu Gly Pro Thr Gly
        595                 600                 605
Val Gly Lys Thr Glu Leu Cys Lys Ala Leu Ala Asn Phe Met Phe Asp
    610                 615                 620
Ser Asp Glu Ala Met Val Arg Ile Asp Met Ser Glu Phe Met Glu Lys
625                 630                 635                 640
His Ser Val Ser Arg Leu Val Gly Ala Pro Pro Gly Tyr Val Gly Tyr
                645                 650                 655
Glu Glu Gly Gly Tyr Leu Thr Glu Ala Val Arg Arg Arg Pro Tyr Ser
            660                 665                 670
Val Ile Leu Leu Asp Glu Val Glu Lys Ala His Pro Asp Val Phe Asn
        675                 680                 685
Ile Leu Leu Gln Val Leu Asp Asp Gly Arg Leu Thr Asp Gly Gln Gly
    690                 695                 700
Arg Thr Val Asp Phe Arg Asn Thr Val Val Ile Met Thr Ser Asn Leu
705                 710                 715                 720
Gly Ser Asp Leu Ile Gln Glu Arg Phe Gly Glu Leu Asp Tyr Ala His
                725                 730                 735
Met Lys Glu Leu Val Leu Gly Val Val Ser His Asn Phe Arg Pro Glu
            740                 745                 750
Phe Ile Asn Arg Ile Asp Glu Val Val Phe His Pro Leu Gly Glu
        755                 760                 765
Gln His Ile Ala Ser Ile Ala Gln Ile Gln Leu Lys Arg Leu Tyr Lys
    770                 775                 780
Arg Leu Glu Glu Arg Gly Tyr Glu Ile His Ile Ser Asp Glu Ala Leu
785                 790                 795                 800
Lys Leu Leu Ser Glu Asn Gly Tyr Asp Pro Val Tyr Gly Ala Arg Pro
                805                 810                 815
Leu Lys Arg Ala Ile Gln Gln Ile Glu Asn Pro Leu Ala Gln Gln
            820                 825                 830
Ile Leu Ser Gly Glu Leu Val Pro Gly Lys Val Ile Arg Leu Glu Val
        835                 840                 845
Asn Glu Asp Arg Ile Val Ala Val Gln
850                 855

<210> SEQ ID NO 2
<211> LENGTH: 7
<212> TYPE: PRT
<213> ORGANISM: Escherichia coli

<400> SEQUENCE: 2

Arg Trp Thr Gly Ile Pro Val
1               5

<210> SEQ ID NO 3
<211> LENGTH: 13
<212> TYPE: PRT
<213> ORGANISM: Homo sapiens

<400> SEQUENCE: 3

Ser Tyr Ser Met Glu His Phe Arg Trp Gly Lys Pro Val
1               5                   10
```

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcagctcgaa ggcaaaacta                                              20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
accgcttcgt tctgaccaat                                              20
```

HAFNIA ALVEI IMPACT ON REGULATION OF APPETITE AND METABOLIC SYNDROME ASPECTS

This application is a continuation-in-part (CIP) application of U.S. Ser. No. 16/032,604 filed Jul. 11, 2018, which is itself a CIP of U.S. Ser. No. 15/101,452, filed Jun. 3, 2016, which is a national stage filing of PCT/EP2014/07661, filed Dec. 4, 2014. This application is also a CIP of U.S. Ser. No. 15/579,459, filed Apr. 5, 2016, which is a national stage filing of PCT/IB2016/051923, filed Apr. 5, 2016. In addition, this application is a CIP application of U.S. Ser. No. 16/091,678 filed Oct. 5, 2018, which is a national stage application of PCT/EP2017/058116, filed Apr. 5, 2017. The complete contents of each of these applications is herein incorporated by reference.

The present invention relates to method of preventing, treating or attenuating obesity-related manifestations in a human or non-human mammal subject in need thereof, said method comprising orally administering to the subject a composition comprising an effective amount of *Hafnia alvei* probiotics; wherein said obesity-related parameters are selected from the group of hyperphagia, increased fat mass on lean mass ratio, increased waist circumference, postprandial hyperglycemia, fasting hyperglycemia and hypercholesterolemia.

Eating disorders increased all over the world among both men and women over the last 50 years. There is evidence to suggest that in particular individuals in the western world are at the highest risk of developing them and the degree of westernization increases the risk. With recent advances, the scientists understand more and more the central processes of appetite. It is known that interactions between motivational, homeostatic and self-regulatory control processes are involved in eating behavior, which is a key component in eating disorders.

Recent science discovered a further regulator, the human microbiome. Advances of high-throughput DNA sequencing technologies allowed to explore the human microbiome and thus to make a major step towards the understanding of the molecular relationships between the host and its microbiota. This "second genome", the microbiome, has been described in a catalogue of more than 4-5 million, non-redundant microbial putative genes and 1 to 2,000 prevalent bacterial species. Each individual has at least 160 shared species and a number of well-balanced host-microbial molecular relationships that defines groups of individuals.

It is considered that understanding the essential features of symbiotic relationships between microbial communities and their human host may allow to predict host phenotypes, such as health status, from the particular features of indigenous communities.

The composition of gut microbiota for example has been associated with host metabolic phenotypes including obesity and diabetes as well as some neuropsychiatric disorders suggesting that gut bacteria may influence brain controlled functions and behavior.

In this context, determining the molecular mechanisms linking the microbiota to the host behavior appears, thus, as a necessary step for defining the role of specific microorganisms in host physiology.

The molecular mechanisms at the origin of eating disorders, including anorexia nervosa (AN), bulimia (BN), and binge-eating disorder (BED), are currently unknown. Previous data indicated that immunoglobulins (Igs) or autoantibodies (auto-Abs) reactive with α-melanocyte-stimulating hormone (α-MSH) are involved in regulation of feeding and emotion; however, the origin of such auto-Abs is unknown.

The inventors discovered, using proteomics, that the ClpB chaperon protein of commensal gut bacteria *E. coli* K12 is a conformational mimetic of α-melanocyte-stimulating hormone (α-MSH), a neuropeptide involved in the regulation of energy metabolism and emotion.

As a consequence, they show that the bacterial ClpB protein, which is present in several commensal and pathogenic microorganisms, can be responsible for the production of auto-Abs crossreactive with α-MSH, associated with altered feeding and emotion in humans with eating disorders.

The inventors having showed that intragastric delivery of *E. coli* and *Hafnia alvei* in mice decreased food intake and body weight gain due to the presence of ClpB protein in bacteria, the invention further relates to a composition comprising probiotics expressing or surexpressing ClpB protein for use in the treatment or prevention of obesity.

The inventors further show that the oral administration of *Hafnia alvei* not only induces weight loss but surprisingly also reduces the fat mass percentage and the hip circumference.

Lastly, contrary to other anti-obesity treatments, the oral administration of *H. alvei* reduces hyperphagia as well as biochemical factors associated to the metabolic syndrome such as elevated glycemia and cholesterol levels.

Thus, the present invention relates to a method of preventing, treating or attenuating obesity-related manifestations in a human or non-human mammal subject in need thereof, said method comprising orally administering to the subject a composition comprising an effective amount *Hafnia alvei* probiotics; wherein said obesity-related parameters are selected from the group of hyperphagia, increased fat mass on lean mass ratio, increased waist circumference, postprandial hyperglycemia, fasting hyperglycemia and hypercholesterolemia.

The subject in need may be obese, or a healthy subject that is overweight.

In one embodiment, the subject has at least one of the following:
- at least 180 or at least 200 mg/dL of total cholesterol and/or at least 100 or at least 130 mg/dL of LDL cholesterol,
- at least 80 or at least 100 mg/dL of glucose at a fasting state.
- at least 80 or at least 90 waist-to-hip ratio (waist circumference).

In one embodiment, *Hafnia alvei* probiotics are administered at a dose between 1000 million and 10000 million UFC.day-1.

*Hafnia alvei* probiotic may be administered to the subject in the form of a pharmaceutical composition or a companion composition to be administered simultaneously or sequentially with a pharmaceutical composition in a method of treatment of a metabolic syndrome condition selected from the group of hyperglycemia, hypercholesterolemia or hepatic disfunction.

Alternatively, *Hafnia alvei* probiotic may be administered to the subject in the form of a nutraceutical or food complement composition.

DETAILED DESCRIPTION OF THE INVENTION

Excess weight conditions are often associated with glucose metabolism dysregulation.

In particular, according to the latest definition of the metabolic syndrome; a subject is diagnosed as suffering from metabolic syndrome if she/he presents central obesity plus any two of following factors: raised fasting plasma glucose, raised triglycerides, reduced HDL cholesterol, and hypertension.

Orlistat (Xenical®, Alli®)) is currently the only available form of prescribed obesity medication which acts on the gastrointestinal system and acts by inhibiting pancreatic lipase and thus reducing fat absorption in the gut which is eliminated in bowel movements.

Nevertheless, the administration of Orlistat has unpleasant side effects including liquid stools, an urgency to go to the toilet, and anal leakage. Furthermore, Orlistat blocks the availability of fat-soluble vitamins such as vitamins A, D, E, and K (Hollywood A. et al. J Obes. 2011: 806896).

The inventors have previously shown that bacteria that expresses the ClpB protein such as for example *Hafnia alvei* are capable of reducing food intake and inducing weight-loss. Surprisingly, compositions comprising the ClpB protein or probiotics expressing the ClpB protein have further direct therapeutic or health enhancing effects.

In fact, the inventors found that the oral administration of *H. alvei* has a positive effect on glucose and cholesterol metabolism.

In a first aspect, the invention relates to a composition, namely a pharmaceutical composition for use as a medicament against glucose metabolism related disorders.

The invention further relates to the composition of the invention for use as a companion composition to be administered simultaneously or sequentially with a pharmaceutical composition in a method of treatment of a metabolic syndrome, namely glucose metabolism-related disorder. The pharmaceutical composition in such method may comprise any one of the known hypoglycemic pharmaceutical agents known in the art. In one embodiment, the pharmaceutical composition comprises a compound selected from insulin, metformin, rosiglitazone, pioglitazone, glipizide, glibenclamide, glimepiride, gliclazide, glycopyramide, gluiquidone, repaglinide, nateglinide, miglitol, acarbose, voglibose, exenatide, liraglutide, lixisenatide, semaglutide, vidagliptin, sitagliptin, saxigliptin, linagliptin, dapaglifozin, canaglifozin or empaglifozin.

Alternatively, the invention relates to a nutraceutical composition for use in a non-therapeutic method for improving the well-being of a subject. In one embodiment, the non-therapeutic method is for improving the glycemic profile of a non-diabetic subject. In one embodiment, the subject is non-obese and non-diabetic. In one embodiment, the subject is a healthy. In one embodiment, the subject is a healthy subject in a prediabetic state.

In one embodiment, the composition of the invention is for use in the prevention and/or the treatment of hyperglycemia or hyperglycemia-related diseases. Disorders related to hyperglycemia comprise but are not limited to obesity, metabolic syndrome, type II diabetes, glucose intolerance, insulin resistance, pre-diabetes, type I diabetes or gestational diabetes.

In one embodiment, the composition of the invention is for use in the prevention and/or the type II diabetes.

In one embodiment, the composition of the invention is for use as companion composition in a method for preventing, treating and/or limiting the diabetic complications in a subject in need thereof. Diabetic complications comprise headache, fatigue, microvascular and macrovascular complications such as blurry vision, slow healing, skin rashes and itchy skin.

In one embodiment, the composition of the invention is for use as companion composition in a method for preventing, treating and/or limiting the chances of developing metabolic syndrome.

In one embodiment, the composition of the invention is for use as companion composition in a method for preventing, treating and/or limiting the glucose intolerance.

In one embodiment, the composition of the invention is for use as companion composition in a method for preventing, reducing the glycated hemoglobin ($HbA_{1C}$) levels the to normal levels, preferably lower than 53 mmol/mol, even more preferably lower than 42 mmol/mol.

The invention further relates to a non-therapeutic method for improving the glucose metabolism of a subject; said method comprising the feeding of the subject with an effective dose of a composition, preferably a nutraceutical composition according to the invention.

In one embodiment, the improving of the glucose metabolism comprises:
lowering the basal glycemia,
lowering the fasting glycemia,
lowering the post-prandial glycemia,
lowering the glycated hemoglobin ($HbA_{1C}$) levels the to normal levels, preferably lower than 53 mmol/mol, even more preferably lower than 42 mmol/mol,
improving the glucose clearance,
improving the glucose tolerance,
improving the response to insulin,
improving the energy balance of the subject,
preventing metabolic syndrome,
maintaining or improving the micro- and macro-vascular condition of the subject.

The invention further relates to a composition, namely a pharmaceutical composition for use as a medicament for preventing and/or treating lipid metabolism related disorders.

The invention further relates to the composition of *H. alvei* for use as a companion composition to be administered simultaneously or sequentially with a pharmaceutical composition in a method of prevention and/or treatment of lipid metabolism-related disorders. The pharmaceutical composition in such method may comprise any one of the known lipid-lowering or anti-hypercholesterolemic pharmaceutical agents known in the art. In one embodiment, the pharmaceutical composition comprises a compound selected from HMG-CoA reductase inhibitors (statins), fibrates, nicotinic acid, cholestyramine, omega-3 fatty acids, phytosterols or phytostanols. In one embodiment, the statins are selected from atorvastatin, fluvastatin, lovastatin, pitavastatin, pravastatin, rosuvastatin, and simvastatin.

In a third aspect, the invention relates to the nutraceutical composition of the invention for use in a non-therapeutic method for improving the well-being of a subject. In one embodiment, the non-therapeutic method is for improving the lipidic profile of a non-diabetic subject. In one embodiment, the subject is non-obese and non-diabetic. In one embodiment, the subject is a healthy. In one embodiment, the subject is a healthy subject in a pre-hyperlipidemic or pre-hypercholesterolemic state.

Hyperlipidemia and hypercholesterolemia are directly associated with cardiovascular diseases. Thus, in one embodiment, the pharmaceutical or nutraceutical composition of the invention is for use in a therapeutic or non-therapeutic method for maintaining or improving the cardiovascular condition of a subject in need thereof. In one embodiment, the subject is a healthy subject. In one embodiment, the subject is suffering from a cardiovascular disorder.

In one embodiment, the subject has already suffered from a cardiovascular disorder such as for example a heart-attack or a thrombosis.

The experimental data further showed a decrease in the cholesterol plasmatic concentration.

In one embodiment, the composition is for use in the prevention and/or the treatment of hypercholesterolemia.

In one embodiment, the composition of the invention is for use in the prevention and/or the treatment of hyperlipidemia.

In one embodiment, the composition is for use in the prevention and/or the treatment of cardiovascular diseases.

In one embodiment, the composition is for use in the prevention and/or the treatment of atherosclerosis.

In one embodiment, the composition is for use in the prevention and/or the treatment of coronary heart disease.

In one embodiment, the composition of the invention is for use as companion composition in a method for preventing, treating and/or limiting the atherosclerotic plaques in a subject in need thereof.

In one embodiment, the composition of the invention is for use as companion composition in a method for preventing, treating and/or limiting the chances of a heart-attack in a subject in need thereof.

In one embodiment, the composition of the invention is for use as companion composition in a method for preventing, treating and/or limiting the chances of a stroke in a subject in need thereof.

In one embodiment, the composition of the invention is for use as companion composition in a method for treating and/or limiting the lipedema in a subject in need thereof.

Lymphatic vessels not only play a physiological role in maintenance of homeostasis and the immune response together with blood vessels, but also participate in the development of pathological states such as inflammation and cancer metastasis In one embodiment, the composition of the invention is for use as companion composition in a method for treating and/or limiting the liquid retention induced by radiotherapy or chemotherapy treatment in a subject suffering from cancer.

In one embodiment, the composition of the invention is for use as companion composition in a method for treating and/or limiting the liquid retention induced by an inflammatory condition in a subject in need thereof.

In one embodiment, the composition of the invention is for use as companion composition in a method for treating and/or limiting the chronic inflammatory condition in a subject in need thereof. In one embodiment, such subject is a subject suffering from metabolic syndrome, preferably suffering from type I or type II diabetes.

The invention further relates to a non-therapeutic method for improving the lipid metabolism of a healthy subject; said method comprising the feeding of the subject with an effective dose of a composition, preferably a nutraceutical composition according to the invention.

In one embodiment, the improving of the lipid metabolism comprises:
lowering the cholesterol plasma concentration,
lowering the very-low-density lipoproteins (VLDL) particles plasma concentration,
raising the high-density lipoprotein (HDL) particles plasma concentration,
lowering the VLDL particles plasma concentration while maintaining or raising the HDL particles plasma concentration,
improving the lipid absorption,
improving the lymphatic drainage, and
limiting the liquid retention.

The invention may further concern therapeutic or non non-therapeutic method for improving the hepatic functions of a subject; said method comprising the feeding of the subject with an effective dose of a composition, preferably a nutraceutical composition according to the invention.

In one embodiment, the improving of the hepatic functions comprises:
lowering the fatigue,
improving the overall metabolism,
improving the response to insulin,
lowering the transaminases plasmatic concentration,
lowering the alkaline phosphatase plasmatic concentration
improving the biliary duct flow, and
decreasing abdominal discomfort, In one embodiment, the composition of the invention is for use as companion composition in a method for preventing, reducing the hepatic enzyme levels the to normal levels. Hepatic enzymes are selected from a list comprising aspartate aminotransferase (AST or SGOT), alanine aminotransferase (known as transaminases), alkaline phosphatase (AP) and gamma-glutamyl transferase (GGT).

In one embodiment, the composition of the invention is for use as companion composition in a method for preventing, treating and/or limiting the chances of developing hepatic dysfunctions.

According to the latest definition of the metabolic syndrome; a subject is diagnosed as suffering from metabolic syndrome if she/he presents central obesity plus any two of following factors: raised triglycerides, reduced HDL cholesterol, hypertension and raised fasting plasma glucose. Therefore, the invention may concern the prevention, treatment or attenuation of any of the aforementioned conditions or metabolic parameters namely glycemic, lipidemic/cholesterol or hepatic parameters.

The inventors have previously discovered, using proteomics, that the ClpB chaperon protein of commensal gut bacteria E. coli K12 is a conformational mimetic of α-melanocyte-stimulating hormone (α-MSH), a neuropeptide involved in the regulation of energy metabolism and emotion and that the presence of ClpB expressing bacteria results in dysregulated appetite.

Accordingly, the present invention refers to a composition comprising at least one antibiotic directed against at least one ClpB expressing bacterium for use in the treatment or prevention of eating disorders.

As used herein, "ClpB expressing bacterium" refers to bacteria expressing the chaperone protein ClpB.

The "protein disaggregation chaperone", "chaperone protein ClpB", "ClpB protein" or "ClpB" also known as heat shock protein F84.1 is a member of the Hsp100/ClpB family of hexameric AAA+-ATPases. This family comprises bacterial, fungal, and plant Hsp100 ATPases, ClpB being the bacterial representative. As a part of a stress-induced multichaperone system, it is involved in the recovery of the cell from heat-induced damage, in cooperation with the Hsp70 system (DnaK, DnaJ and GrpE) in protein disaggregation, a crucial process for cell survival under stress conditions.

During the infection process, bacterial pathogens encounter stress conditions generated by the host defense to eliminate them and respond to this host defense by increasing the synthesis of heat shock and other stress proteins. In this context, ClpB has been described as an essential factor for acquired thermotolerance and for the virulence and infectivity of several Gram-negative and Gram-positive pathogenic bacteria, such as *Staphylococcus aureus, Francisella turalensis, Listeria monocytogenes, Yersinia enterocolitica,* and *Salmonella thyphimurium.*

In *E. coli* K12 the chaperone protein ClpB also known as heat shock protein F84.1 or htpM and is a protein of 857 amino acids.

Typically, the chaperone protein ClpB comprises or consists of the amino acid sequence of the chaperone protein ClpB from *E. coli* K12 with SEQ ID NO: 1 (NCBI Reference Number: NP_417083.1, as available on Nov. 6, 2013 and/or UniProtKB/Swiss-Prot Number: P63284, as available on Nov. 6, 2013). Preferably, the amino acid sequence of chaperone protein ClpB comprises or consists of an amino acid sequence 80 to 100% identical to the amino acid sequence of SEQ ID NO: 1. Preferably, the amino acid sequence is 90 to 100% identical, more preferably 95 to 100%, most preferably 95, 96, 97, 98, 99 or 100% identical to the amino acid sequence of SEQ ID NO: 1.

Thus, a ClpB expressing bacterium refers to a bacterium expressing or overexpressing the chaperone protein ClpB as defined above or a polypeptide comprising or consisting of an amino acid sequence 80 to 100% identical to the amino acid sequence of SEQ ID NO: 1, more preferably 95 to 100%, most preferably 95, 96, 97, 98, 99 or 100% identical to the amino acid sequence of SEQ ID NO: 1.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the context of the present application, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is, for example, available on the ebi.ac.uk world wide web site. The percentage of identity in accordance with the invention is preferably calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

Amino acid substitutions may be conservative or non-conservative. Preferably, substitutions are conservative substitutions, in which one amino acid is substituted for another amino acid with similar structural and/or chemical properties. The substitution preferably corresponds to a conservative substitution as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

ClpB expressing bacteria are well-known from the skilled person and may be identified by any conventional technique such as by bacterial stress-induction or genetic engineering.

In some embodiments, the bacterial strain, in particular the probiotic bacterial strain, is a gram-negative strain.

In one embodiment, the bacterial strain, in particular the probiotic bacterial strain, is a non-pathogenic gram-negative strain.

In one embodiment, the ClpB expressing bacterium is selected from the group constituted of the genus *Staphylococcus aureus, Francisella turalensis, Listeria monocytogenes, Yersinia enterocolitica, Salmonella thyphimurium, Escherichia Coli, Enterobacteriaceae, Shigella sonnei, Shigella flexneri, Shigella dysenteriae, Shigella boydii, Citrobacter youngae, Salmonella bongori* and *Salmonella enterica.*

In one embodiment, the ClpB expressing bacterium is selected from the group constituted of the taxa *Staphylococcus aureus, Francisella turalensis, Listeria monocytogenes, Yersinia enterocolitica, Salmonella thyphimurium, Escherichia Coli, Enterobacteriaceae, Citrobacter youngae, Salmonella bongori* and *Salmonella enterica.*

In some embodiments, the bacterial strain, in particular the probiotic bacterial strain, is a member of the family of Enterobacteriaceae.

In particular, the bacterial strain is a non-pathogenic member of the family of Enterobacteriaceae. In one embodiment, the ClpB expressing bacterium is selected from the group constituted of the genera *Escherichia Coli, Citrobacter youngae, Proteus, Klebsiella, Hafnia, Providencia* and *Enterobacter.*

In one embodiment, the ClpB expressing bacterium is selected from the group constituted of the genera *Escherichia, Proteus* and *Hafnia.*

In some embodiments, the bacterial strain, in particular the probiotic bacterial strain, is an *E. coli* strain. In some embodiments, *E. coli* strains, in particular probiotic *E. coli* strains, for use according to the teachings of present invention include non-pathogenic *E. coli* strains which exert probiotic activity. Example of probiotic *E. coli* strain is the probiotic *Escherichia coli* strain BU-230-98, ATCC Deposit No. 202226 (DSM 12799), which is an isolate of the known, commercially available, probiotic *Escherichia coli* strain M-17. Example of a non-pathogenic *E. coli* strain is *E. coli* Nissle 1917. An example of *E. coli* strain which was not known as probiotic is the laboratory *E. coli* strain K12.

In other embodiments, the bacterial strain is a *Hafnia alvei* strain, such as the *Hafnia alvei* strain AF036 commercialized by Bioprox Company. In other embodiments, the bacterial strain is a *Hafnia alvei* strain, such as the *Hafnia alvei* strain AF036 or HA commercialized by Bioprox Company or HA4597 by Biodis company.

In still other embodiments, a combination of bacterial strains expressing or overexpressing the ClpB protein or variant thereof is used.

The ClpB protein comprises two nucleotide binding domains (ATP1 and ATP2) and two oligomerization domains (NBD1 and NBD2). The N-terminal domain might function as a substrate-discriminating domain, recruiting aggregated proteins to the ClpB hexamer and/or stabilizing bound proteins. The NBD2 domain is responsible for oligomerization, whereas the NBD1 domain stabilizes the hexamer probably in an ATP-dependent manner. The movement of the coiled-coil domain is essential for ClpB ability to rescue proteins from an aggregated state, probably by pulling apart large aggregated proteins, which are bound between the coiled-coils motifs of adjacent ClpB subunits in the functional hexamer.

The inventors identified that the ClpB chaperon protein of commensal gut bacteria E. coli K12 is a conformational mimetic of α-melanocyte-stimulating hormone (α-MSH), a neuropeptide involved in the regulation of energy metabolism and emotion.

"α-MSH", also known as "α-Melanocyte-stimulating hormone", "alpha-MSH", "α-MSH", alpha-melanotropin, alpha-melanocortin, or alpha-intermedin, is a naturally occurring endogenous peptide hormone of the melanocortin family, with a tridecapeptide structure. The amino acid sequence of α-MSH preferably comprises or consists of the amino acid sequence SYSMEHFRWGKPV (SEQ ID NO: 3) (Gen Pept Sequence ID, PRF: 223274, as available on Dec. 2, 2013). However, there exist three types of alpha-melanocyte-stimulating hormone that differ in their acetyl status, the desacetyl alpha MSH, which lacks an acetyl group; mono-acetyl alpha MSH, in which the amino group of the Ser-1 of SEQ ID NO: 3 is acetylated; and di-acetyl alpha MSH, in which both amino and hydroxy groups of the Ser-1 of SEQ ID NO: 3 are acetylated. α-MSH as used herein refers in particular to the mono-acetylated α-MSH.

It is critically involved in the regulation of energy balance and increasing energy expenditure via activation of the melanocortin receptors type 4 (MC4R), acting both centrally and peripherally. In both humans and mice, plasma α-MSH levels are associated with body weight changes. Furthermore, α-MSH regulates mood and emotion by increasing anxiety.

"Mimetic" refers to a protein that imitates another protein. This imitation is possible since the protein shares certain characteristics with the protein it mimetics.

A "conformational mimetic" refers to a protein, that shares at least in part the same conformation as another protein.

The inventors demonstrated that the ClpB protein shares a discontinuous sequence homology between amino acids 542 to 548 from SEQ ID NO: 1 with α-MSH, of amino acid sequence 'RWTGIPV' (referenced under SEQ ID NO: 2). Without being bound by theory, this conformation of ClpB allows stimulating the production of antibodies directed against both ClpB and α-MSH.

Thus "conformational mimetic" herein preferably refers to the capability to stimulate antibody production against ClpB as well as auto antibodies against α-MSH.

In the context of the invention, the term "treating" or "treatment", as used herein, means reversing, alleviating, inhibiting the progress of the disorder to which such term applies, or one or more symptoms of such disorder or condition. In one embodiment, treating or preventing correspond to attenuating or reducing the value of a biochemical parameter such as fasting glycemia, total cholesterol, or LDL-cholesterol. In one embodiment, attenuating refers to reducing the biochemical parameter value by at least 1%; at least 2% or at least 5% compared to said value prior to the initiation of the administration according to the present invention. In one embodiment, attenuating refers to reducing the waist-to-hip ratio by at least 1%; at least 2% or at least 5% compared to said value prior to the initiation of the administration according to the present invention.

"Preventing" refers to measures taken to prevent the disorder to which such term applies from occurrence or, in early stages of a disorder. Preventing further refers to the inhibition of further development of a disorder to which such term applies.

Treatment or prevention of eating disorders preferably refers herein to the reduction of the amount or concentration of ClpB expressing bacteria in the subject to be treated.

In the context of the present invention, a "subject" denotes a human or non-human mammal, such as a rodent (rat, mouse, rabbit), a primate (chimpanzee), a feline (cat), or a canine (dog). Preferably, the subject is human. The subject according to the invention may be in particular a male or a female.

In some embodiments, the subject is an adult (for example, a human subject above the age of 18). In another embodiment, the subject is a child (for example, a human subject below the age of 18). In some embodiments, the subject may be a "patient", i.e. a subject who/which is awaiting the receipt of, or is receiving medical care or was/is/will be the object of a medical procedure according to the methods of the present invention, or is monitored for the development of a disease.

In some embodiments, the subject has a body mass index of between 18.5 and 30.

In the context of this invention, subject is obese and has a BMI superior to 30.

In some embodiments, the subject is moderately obese. A "moderately obese" subject refers to a subject having a BMI of between 30 and 35.

Preferably, the subject according to the invention is older than 13.

Preferably, the subject is a female.

By "eating disorder" (ED) is meant psychiatric illnesses defined by criteria from the Diagnostic and Statistical Manual of Mental Disorders 5th Edition (DSM-5) and earlier editions (DSM-4, etc). Abnormal eating habits may involve either insufficient or excessive food intake to the detriment of an individual's physical and mental health. Bulimia nervosa (BN), anorexia nervosa (AN) and binge eating disorder (BED) are the most common specific forms of eating disorders. According to the DSM-5 criteria, to be diagnosed as having anorexia nervosa a person must display: persistent restriction of energy intake leading to significantly low body weight (in context of what is minimally expected for age, sex, developmental trajectory, and physical health), either an intense fear of gaining weight or of becoming fat, or persistent behavior that interferes with weight gain (even though significantly low weight), disturbance in the way one's body weight or shape is experienced, undue influence of body shape and weight on self-evaluation, or persistent lack of recognition of the seriousness of the current low body weight.

According to the DSM-5 criteria, to be diagnosed as having bulimia nervosa a person must display recurrent episodes of binge eating. An episode of binge eating is characterized by both of the following: eating, in a discrete period of time (e.g. within any 2-hour period), an amount of food that is definitely larger than most people would eat during a similar period of time and under similar circumstances and a sense of lack of control over eating during the episode (e.g. a feeling that one cannot stop eating or control what or how much one is eating), recurrent inappropriate compensatory behavior in order to prevent weight gain, such as self-induced vomiting, misuse of laxatives, diuretics, or other medications, fasting, or excessive exercise. The binge eating and inappropriate compensatory behaviors both occur, on average, at least once a week for three months. Self-evaluation is unduly influenced by body shape and weight.

According to the DSM-5 criteria, to be diagnosed as having binge eating disorder a person must display recurrent episodes of binge eating. An episode of binge eating is characterized by both of the following: eating, in a discrete period of time (e.g. within any 2-hour period), an amount of food that is definitely larger than most people would eat during a similar period of time and under similar circumstances, a sense of lack of control over eating during the episode (e.g. a feeling that one cannot stop eating or control what or how much one is eating). The binge eating episodes are associated with three or more of the following:
- eating much more rapidly than normal;
- eating until feeling uncomfortably full;
- eating large amounts of food when not feeling physically hungry;
- eating alone because of feeling embarrassed by how much one is eating;
- feeling disgusted with oneself, depressed or very guilty afterward.

Binge eating occurs, on average, at least once a week for three months.

Other types of eating disorders include Other Specified Feeding or Eating Disorder (OSFED).

According to the DSM-5 criteria, to be diagnosed as having OSFED a person must present with a feeding or eating behaviors that cause clinically significant distress and impairment in areas of functioning, but do not meet the full criteria for any of the other feeding and eating disorders. A diagnosis might then be allocated that specifies a specific reason why the presentation does not meet the specifics of another disorder (e.g. bulimia nervosa-low frequency). The following are further examples for OSFED:
- Atypical anorexia nervosa: all criteria are met, except despite significant weight loss, the individual's weight is within or above the normal range;
- Binge eating disorder (of low frequency and/or limited duration): all of the criteria for BED are met, except at a lower frequency and/or for less than three months;
- Bulimia nervosa (of low frequency and/or limited duration): all of the criteria for bulimia nervosa are met, except that the binge eating and inappropriate compensatory behavior occurs at a lower frequency and/or for less than three months;
- Purging disorder: recurrent purging behavior to influence weight or shape in the absence of binge eating;
- Night eating syndrome: recurrent episodes of night eating, eating after awakening from sleep, or by excessive food consumption after the evening meal. The behavior is not better explained by environmental influences or social norms. The behavior causes significant distress/impairment. The behavior is not better explained by another mental health disorder (e.g. BED); Unspecified Feeding or Eating Disorder (UFED). According to the DSM-5 criteria this category applies to where behaviors cause clinically significant distress/impairment of functioning, but do not meet the full criteria of any of the Feeding or Eating Disorder criteria. This category may be used by clinicians where a clinician chooses not to specify why criteria are not met, including presentations where there may be insufficient information to make a more specific diagnosis (e.g. in emergency room settings). In the context of the present invention, an eating disorder can thus refer to the above mentioned list of disorders.

In one embodiment, the eating disorder is selected from the group consisting of anorexia nervosa (AN), bulimia nervosa (BN), binge eating disorder (BED), overeating, hyperphagia, wasting diseases such as cachexia By "appetite" is meant the desire to eat food, felt as hunger. Appetite exists in all higher life-forms, and serves to regulate adequate energy intake to maintain metabolic needs. It is regulated by a close interplay between the digestive tract, energy storage such as in adipose tissue and liver and the brain. Appetite is assessed in a subject by measuring the amount of food ingested and by assessing the subject's desire to eat.

"Dysregulation of appetite" refers to an abnormal appetite which includes increased appetite overeating, binge eating disorder and hyperphagia.

The "BMI" or "body mass index" is defined as the subject's body mass divided by the square of his height. The formulae universally used in medicine produce a unit of measure of $kg/m^2$.

"Bulimia" or "Bulimia nervosa" is an eating disorder characterized by binge eating and purging, or consuming a large amount of food in a short amount of time followed by an attempt to rid oneself of the food consumed (purging), typically by vomiting, taking a laxative or diuretic, and/or excessive exercise. Some subjects may tend to alternate between bulimia nervosa and anorexia nervosa. Subject suffering from bulimia may be characterized by a normal BMI range, usually inferior to 25.

"Binge eating disorder" or "BED" refers to an eating disorder characterized by binge eating consisting of eating, in a discrete period of time (e.g. within any 2-hour period), an amount of food that is larger than most people would eat in a similar period of time under similar circumstances, and is accompanied by a feeling of loss of control. The binge eating occurs, on average, at least twice a week for 6 months. Contrary to bulimia the binge eating is not associated with the recurrent use of inappropriate compensatory behavior. Subjects suffering from BED are seriously worried about the binge eating. Furthermore, subjects suffering from BED eat until being physically uncomfortable and nauseated due to the amount of food consumed and/or eat when bored or depressed and/or eat large amounts of food even when not really hungry and/or eat alone during periods of normal eating, owing to feelings of embarrassment about food and/or feel disgusted, depressed, or guilty after binge eating. Subjects with binge eating disorder act impulsively and feel a lack of control over their eating. Furthermore, subject suffering from binge eating disorder have problems coping with stress, anxiety, anger, sadness, boredom and worry.

In the context of this invention, subjects suffering of BED are preferably obese and have a BMI superior to 30.

"Overeating" is the consumption of excess food in relation to the energy that an organism expends (or expels via excretion), leading to weight gaining. Overeating can sometimes be a symptom of binge eating disorder or bulimia. Compulsive over eaters depend on food to comfort themselves when they are stressed, suffering bouts of depression, and have feelings of helplessness.

"Hyperphagia", also known as "polyphagia" refers to excessive hunger (compulsive) or increased appetite. In one embodiment hyperphagia may be caused by disorders such as Diabetes, Kleine-Levin Syndrome, the genetic disorders Prader-Willi Syndrome and Bardet Biedl Syndrome.

"Wasting disease" refers to the process by which a debilitating disease causes muscle and fat tissue to "waste" away. Wasting can be caused by an extremely low energy intake (e.g., caused by famine), nutrient losses due to infection, or a combination of low intake and high loss.

"Cachexia" is a wasting syndrome associated with loss of weight and/or muscle atrophy and/or fatigue, weakness, and significant loss of appetite which may be caused by cancer, AIDS, chronic obstructive lung disease, multiple sclerosis, congestive heart failure, tuberculosis, familial amyloid polyneuropathy, mercury poisoning (acrodynia) and hormonal deficiency. Cachexia, or wasting, as it may also be called, is seen with several diseases, such as AIDS, cancer, post hip fracture, chronic heart failure, chronic lung disease such as chronic obstructive lung disease (COLD) and/or chronic obstructive pulmonary disease (COPD), liver cirrhosis, renal failure, and autoimmune diseases such as rheumatoid arthritis and systemic lupus, sepsis and severe infection. Furthermore, wasting is also seen in aging.

In some embodiments, cachexia is caused by cancer.

The foremost sign of cachexia is weight loss, not only of fatty tissue but also of muscle tissue and even bone. This non-fatty tissue is also known as "lean body mass."

In addition, there is loss of appetite, weakness (asthenia), and a drop in hemoglobin level (anemia).

Cachexia is found as the terminal state of many different clinical conditions or in chronic diseases such as cancer, infections, AIDS, congestive heart failure, rheumatoid arthritis, tuberculosis, post-hip fracture, cystic fibrosis and Crohn's disease. It can also occur in elderly people who do not have any obvious symptoms of disease.

"Increased appetite" refers to an appetite wherein a subject has a higher food intake than the body requires. This may or may not result in weight gain.

"Normal appetite" thus refers to a subject having a food intake that corresponds to the amount of food the body requires.

"Decreased appetite" and/or "reduced appetite" refers an appetite wherein a subject has a lower food intake than the body requires. This may or may not result in weight loss.

"Food intake" can be measured using a multitude of techniques including self-reporting using e.g. diaries or questionnaires, measurements of calorie-intake from a buffet meal, using weighing of food prior to ingestion, or weighing and analysis of paired quantities of food. The food intake may be measured on a meal basis, a daily basis, a weekly basis or a monthly basis.

In one embodiment the composition is for decreasing weight gain in the subject.

The composition may be used, for example, to decrease appetite, wherein the increased appetite is due to binge eating disorder or overeating (hyperphagia).

In an embodiment of the invention, the treatment results in at least 1% decrease in food intake, such as a decrease of 2%, more preferably 3% or 5% or 7%, and even more preferred 10% below average food intake prior to initiation of treatment.

In another embodiment, the treatment leads to decrease in calorie intake irrespective of changes in food intake, since amount of food ingested may not be directly related to the ingested calorie intake, as the various food items such as fat, carbohydrates and proteins contain different amounts of calories per amount food.

In an embodiment of the invention, the treatment results in a at least 1% decrease in calorie intake, such as a decrease of 2%, more preferably 3%, or 5% or 7%, and even more preferred a decrease of 10% in calorie intake below average calorie intake prior to initiation of treatment.

A subject in need thereof is a subject suffering from an eating disorder, as herein defined, in particular selected from the group consisting of anorexia nervosa (AN), bulimia nervosa (BN), binge eating disorder (BED), hyperphagia, wasting diseases such as cachexia, and more particularly from anorexia nervosa (AN), bulimia nervosa (BN) and binge eating disorder (BED).

Also provided is the use of a composition comprising at least one antibiotic directed against at least one ClpB expressing bacterium for the manufacture of a medicament intended for the treatment or prevention of eating disorders, as herein defined.

The inventors discovered that disregulated appetite is associated with the presence of ClpB protein and/or anti-ClpB antibodies and increased plasma levels of anti-α-MSH-reactive antibodies, preferably anti-ClpB IgG and/or IgM and anti-α-MSH-reactive IgG and/or IgM.

In one embodiment, the composition used in the context of the invention is a pharmaceutical composition.

Pharmaceutical compositions used in the context of the invention are preferably designed to be appropriate for the selected mode or route of administration, and pharmaceutically acceptable diluents, carriers, and/or excipients such as dispersing agents, buffers, surfactants, preservatives, solubilizing agents, isotonicity agents, stabilizing agents, and the like are used as appropriate. Such compositions can be designed in accordance with conventional techniques as disclosed, for example, in Remington, The Science and Practice of Pharmacy, 19th Edition, Gennaro, Ed., Mack Publishing Co., Easton, Pa. 1995.

Suitable carriers for pharmaceutical compositions include any material which, when combined with the antibiotic of the invention retains the molecule's activity and is non-reactive with the subject's immune system.

The pharmaceutical compositions according to the invention may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels.

The mode of administration and dosage forms are closely related to the properties of the therapeutic agents or compositions which are desirable and efficacious for the given treatment application. Suitable dosage forms include, but are not limited to, oral, rectal, sublingual, mucosal, nasal, and other dosage forms for systemic delivery of active ingredients.

Pharmaceutical compositions of the invention may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations; conjunctival (eyedrops); rectal (suppository, enema)); or intradermal (bolus, infusion, depot).

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

Pharmaceutical compositions of the invention may also contain excipient such as flavorings, colorings, anti-microbial agents, or preservatives.

The administration regimen may be for instance for a period of at least 2, 3, 4, 5, 6, 7, 8, 9, 10, 15, 20, 25, 30, 35, 40, 45, 50, 55, 60, 65, 70, 75, 80, 85, 90, 95, 100 days.

The dose range depends on the composition to be administered and is defined above.

As is well known in the medical arts, dosages for any one subject depend on many factors, including the patient's size, body surface area, age, the particular compound to be administered, sex, time and route of administration, general health, and other drugs being administered concurrently.

Overweight or too low body weight might also be considered in certain cultures as a physical appearance that is considered to be less attractive.

All the definitions previously mentioned also apply to the said non therapeutical method.

In one embodiment, an effective amount or a therapeutically effective amount is at least the minimal dose, but less than a toxic dose, of an active agent which is necessary to impart therapeutic benefit or benefit to a subject. Stated another way, such an amount for treating eating disorders, for example, is an amount that induces, ameliorates, or otherwise causes an improvement in the state of the subject, as the regulation of food intake.

In one embodiment said non-therapeutic method is a cosmetic method.

As mentioned above, the invention also relates to a composition comprising probiotics not expressing ClpB protein for use in the treatment or prevention of an eating disorder.

All the definitions previously mentioned also apply to the said composition.

In one embodiment, the eating disorder is selected from the group consisting of anorexia nervosa (AN), bulimia nervosa (BN), binge eating disorder (BED), hyperphagia, wasting diseases such as cachexia, and more particularly from anorexia nervosa (AN), bulimia nervosa (BN) and binge eating disorder (BED).

It further relates to a non-therapeutic method of regulating appetite in a subject, comprising administering to said subject an effective amount of a composition comprising probiotics not expressing ClpB protein.

All the definitions previously mentioned also apply to the said non therapeutical method.

By "probiotic" is meant a food additive comprising an effective amount of a microorganism, intended to be introduced in the diet. According to WHO, probiotics are live microorganisms which, when administered in adequate amounts confer a benefit to the host health (WHO, 2001). As used herein, the expression "probiotic bacterial strain" denotes a bacterial strain that has a beneficial effect on the health and well-being of the host.

In the context of the invention, the bacterium introduced in the diet is a bacterium expressing or not expressing ClpB protein. The latter being a bacterium normally expressing the ClpB protein in which the expression of the protein would have been deleted.

In a preferred embodiment, the probiotic strain expresses or overexpresses the ClpB protein. In a particularly preferred embodiment of the invention, the probiotic strain expresses or overexpresses the ClpB protein is *Hafnia alvei*.

ClpB expressing bacteria are well-known from the skilled person and may be identified by any conventional technique.

As used herein, the term "biological sample" means a substance of biological origin. Examples of biological samples include, but are not limited to blood, plasma, serum or saliva. Preferably, a biological sample according to the present invention is a blood, serum and/or plasma sample, in particular plasma sample. The biological sample according to the invention may be obtained from the subject by any appropriate means of sampling known from the skilled person.

The inventors having showed that chronic intragastric delivery of *E. coli* in mice decreased food intake, the invention further relates to a composition comprising probiotics overexpressing ClpB protein for use in the treatment or prevention of obesity.

"Obesity" refers herein to a medical condition wherein the subject preferably has a BMI superior to 30.

By "overexpressing" is meant the artificial expression of a protein due to expression of a gene in increased quantity, here the increased expression of the gene encoding for ClpB protein.

In some embodiments, the bacterial strain, in particular probiotic bacterial strain, of the present invention is a bacterium which constitutively expresses the ClpB protein or variant thereof.

In some embodiments, the ClpB protein or variant thereof is overexpressed in the bacterium. Generally, a protein expression is "upregulated" or a protein is "over-expressed" when it is expressed or produced in an amount or yield that is higher than a given base-line yield that occurs in nature at standard conditions. Over-expression of a protein can be achieved, for example, by altering any one or more of: (a) the growth or living conditions of the host cells; (b) the polynucleotide encoding the protein; (c) the promoter used to control expression of the polynucleotide and its copy number in the cell; and (d) the host cells themselves.

In some embodiments, the bacterium is subjected to stress conditions so that the expression of the ClpB protein or variant thereof is up regulated in the bacterium. Stress may be selected from the group consisting of an exposure to heat, temperature changes, mechanical stress, or long term storage, low moisture storage and/or freeze drying or spray drying.

In some embodiments, the ClpB protein or variant thereof is overexpressed in the bacterium. Generally, a protein expression is "upregulated" or a protein is "over-expressed" when it is expressed or produced in an amount or yield that is higher than a given base-line yield that occurs in nature at standard conditions. Over-expression of a protein can be achieved, for example, by altering any one or more of: (a) the growth or living conditions of the host cells; (b) the polynucleotide encoding the protein; (c) the promoter used to control expression of the polynucleotide and its copy number in the cell; and (d) the host cells themselves.

In some embodiments, the bacterium was subjected to stress conditions so that the expression of the ClpB protein or variant thereof is up regulated in the bacterium. Stress may be selected from the group consisting of an exposure to heat, temperature changes, mechanical stress, or long term storage, low moisture storage and/or freeze drying or spray drying.

A bacteria overexpressing ClpB protein can be prepared by methods known to the skilled person. This can for example be done by bacterial transformation with vectors expressing ClpB DNA.

In some embodiments, the bacterial strain, in particular the probiotic bacterial strain, of the present invention is a bacterium which has been genetically engineered for expressing the ClpB protein or variant thereof. Typically, the bacterial strain was transformed with a nucleic acid encoding for the ClpB protein or variant thereof. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acid may remain extra-chromosomal upon transformation of a parental microorganism or may be adapted for integration into the genome of the microorganism. Accordingly, the nucleic acid may include additional nucleotide sequences adapted to assist integration (for example, a region which allows for homologous recombination and targeted integration into the host genome) or stable expression and replication of an extrachromosomal construct (for example, origin of replication, promoter and other regulatory sequences). In some embodiments, the nucleic acid is nucleic acid construct or vector. In some embodiments, the nucleic acid construct or vector is an expression construct or vector, however other constructs and vectors, such as those used for cloning are encompassed by the invention. In some embodiments, the expression construct or vector is a plasmid. Typically, the expression construct/vector further comprises a promoter, as herein before described. In some embodiments, the promoter allows for constitutive expression of the genes under its control. However, inducible promoters may also be employed. It will be appreciated that an expression construct/vector of the present invention may contain any number of regulatory elements in addition to the promoter as well as additional genes suitable for expression of the ClpB protein or variant thereof if desired. Methods for transforming bacterial cell with extracellular nucleic acids are well known in the art.

In one embodiment, the ClpB overexpressing bacterium is selecting from bacteria known as probiotic or commensal non-pathogenic bacteria in humans, e.g. non-pathogenic *Escherichia coli*.

By "effective amount" is meant an amount of bacteria that allows the manifestation of the desired effect. In particular, it is meant an amount of between 1000 million and 10000 million UFC.day-1. In one embodiment, *H. alvei* is administered at least once, preferably at least twice a day.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

In a particular embodiment, the bacterial strain of the invention is lyophilized, then preferably resuspended before being administered.

Typically, the bacterial strain, in particular the probiotic bacterial strain, of the present invention is administered to the subject by ingestion (i.e. oral route).

In one embodiment, the bacterial strain, in particular the ClpB expressing or overexpressing strain is formulated in a pharmaceutical or nutraceutical formulation.

In some embodiments, the bacterial strain, in particular the probiotic bacterial strain, of the present invention is encapsulated in order to be protected against the stomach. Accordingly, in some embodiments the bacterial strain, in particular the probiotic bacterial strain, of the present invention is formulated in compositions in an encapsulated form so as significantly to improve their survival time. In such a case, the presence of a capsule may in particular delay or prevent the degradation of the microorganism in the gastrointestinal tract. It will be appreciated that the compositions of the present embodiments can be encapsulated into an enterically-coated, time-released capsule or tablet. The enteric coating allows the capsule/tablet to remain intact (i.e., undissolved) as it passes through the gastrointestinal tract, until such time as it reaches the small intestine. Methods of encapsulating live bacterial cells are well known in the art (see, e.g., U.S. patents to General Mills Inc. such as U.S. Pat. No. 6,723,358). For example, micro-encapsulation with alginate and Hi-Maize™ starch followed by freeze-drying has been proved successful in prolonging shelf-life of bacterial cells in dairy products [see, e.g., Kailasapathy K. (2002) Curr Issues Intest Microbiol 3(2), 39-48]. Alternatively, encapsulation can be done with glucomannane fibers such as those extracted from Amorphophallus konjac. Alternatively, entrapment of viable bacteria in sesame oil emulsions may also be used [see, e.g., Hou R. C., Lin M. Y., Wang M. M., Tzen J. T. (2003) J Dairy Sci 86, 424-428]. In some embodiments, agents for enteric coatings are preferably methacrylic acid-alkyl acrylate copolymers, such as Eudragit® polymers. Poly(meth)acrylates have proven particularly suitable as coating materials. EUDRAGIT® is the trade name for copolymers derived from esters of acrylic and methacrylic acid, whose properties are determined by functional groups. The individual EUDRAGIT® grades differ in their proportion of neutral, alkaline or acid groups and thus in terms of physicochemical properties. The skillful use and combination of different EUDRAGIT® polymers offers ideal solutions for controlled drug release in various pharmaceutical and technical applications. EUDRAGIT® provides functional films for sustained-release tablet and pellet coatings. The polymers are described in international pharmacopeias such as Ph.Eur., USP/NF, DMF and JPE. EUDRAGIT® polymers can provide the following possibilities for controlled drug release: gastrointestinal tract targeting (gastroresistance, release in the colon), protective coatings (taste and odor masking, protection against moisture) and delayed drug release (sustained-release formulations). EUDRAGIT® polymers are available in a wide range of different concentrations and physical forms, including aqueous solutions, aqueous dispersion, organic solutions, and solid substances. The pharmaceutical properties of EUDRAGIT® polymers are determined by the chemical properties of their functional groups. A distinction is made between:

poly(meth)acrylates, soluble in digestive fluids (by salt formation) EUDRAGIT® L (Methacrylic acid copolymer), S (Methacrylic acid copolymer), FS and E (basic butylated methacrylate copolymer) polymers with acidic or alkaline groups enable pH-dependent release of the active ingredient. Applications: from simple taste masking via resistance solely to gastric fluid, to controlled drug release in all sections of the intestine.

poly(meth)acrylates, insoluble in digestive fluids: EUDRAGIT® RL and RS (ammonio methacrylate copolymers) polymers with alkaline and EUDRAGIT® NE polymers with neutral groups enable controlled time release of the active by pH-independent swelling.

Enteric EUDRAGIT® coatings provide protection against drug release in the stomach and enable controlled release in the intestine. The dominant criterion for release is the pH-dependent dissolution of the coating, which takes place in a certain section of the intestine (pH 5 to over 7) rather than in the stomach (pH 1-5). For these applications, anionic EUDRAGIT® grades containing carboxyl groups can be mixed with each other. This makes it possible to finely adjust the dissolution pH, and thus to define the drug release site in the intestine. EUDRAGIT® L and S grades are suitable for enteric coatings. EUDRAGIT® FS 30 D (aqueous dispersion of an anionic copolymer based on methyl acrylate, methyl methacrylate and methacrylic acid) is specifically used for controlled release in the colon.

Typically, the bacterial strain, in particular the probiotic bacterial strain, of the present invention is administered to the subject in the form of a pharmaceutical, nutraceutical or food composition. Accordingly, one further aspect of the present invention relates to a pharmaceutical, nutraceutical or food composition comprising an amount of the bacterial strain, in particular the probiotic bacterial strain, of the present invention.

In some embodiments, the food composition that comprises the bacterial strain, in particular the probiotic bacterial strain, of the present invention is selected from complete food compositions, food supplements, nutraceutical compositions, and the like. The composition of the present invention may be used as a food ingredient and/or feed ingredient.

The hereinabove described formulations can be in the form of a solution or as a solid, depending on the use and/or the mode of application and/or the mode of administration.

In one embodiment, the bacterial strain, in particular the probiotic bacterial strain, of the present invention is typically added at any time during the production process of the composition, e.g. they may be added to a food base at the beginning of the production process or they may be added to the final food product.

The composition that comprises the bacterial strain, in particular the probiotic bacterial strain, of the present invention may be solid, semi-solid or liquid. It may be in the form of a medicament, a food product or food supplement, e.g. in the form of tablets, gels, powders, capsules, drinks, bars, etc. For example, the composition may be in the form of a powder packed in a sachet which can be dissolved in water, fruit juice, milk or another beverage.

"Pharmaceutical composition" refers to a composition comprising an active principle in association with a pharmaceutically acceptable vehicle or excipient. A pharmaceutical composition is for therapeutic use, and relates to health. Especially, a pharmaceutical composition may be indicated for treating or preventing obesity. According to the invention, the term "treating a disease" refers to reducing or alleviating at least one adverse effect, disorder or symptom related to obesity. The expression "Preventing a disease" or "Inhibiting the development of a disease" refers to preventing or avoiding the occurrence of obesity and associated adverse effects, disorders or symptoms.

As used herein, the term "food ingredient" or "feed ingredient" includes a formulation which is or can be added to functional foods or foodstuffs as a nutritional supplement.

By "nutritional food" or "nutraceutical" or "functional" food, is meant a foodstuff which contains ingredients having beneficial effects for health or capable of improving physiological functions.

By "food supplement", is meant a foodstuff having the purpose of completing normal food diet. A food supplement is a concentrated source of nutrients or other substances having a nutritional or physiological effect, when they are taken alone or as a combination in small amounts.

According to the invention, "functional food" summarizes foodstuff and corresponding products lately developed to which importance is attributed not only due to them being valuable as to nutrition and taste but due to particular ingredient substances. According to the invention, the middle- or long-term maintenance and promotion of health are of importance. In this context, non-therapeutic uses are preferred. The terms "nutraceuticals", "foodsceuticals", "food complements" and "designer foods", which also represent embodiments of the invention, are used as synonyms, partly, however, also in a differentiated way. The preventive aspect and the promotion of health as well as the food character of the products are, however, best made clear by the term functional food. In many cases, these relate to products accumulated by assortment and selection (as is also the case in the present invention), purification, concentration, increasingly also by addition. Isolated effective substances, in particular in form of tablets or pills, are not included. Although there is no legal definition of a functional food, most of the parties with an interest in this area agree that they are foods marketed as having specific health effects beyond basic nutritional effects. Accordingly, functional foods are ordinary foods that have components or ingredients (such as those described herein) incorporated into them that impart to the food a specific functional e.g. medical or physiological benefit other than a purely nutritional effect.

In some embodiments, the drink is a functional drink or a therapeutic drink, a thirst-quencher or an ordinary drink. By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavored filling, fruit flavored cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

In some embodiments, the composition that comprises the bacterial strain, in particular the probiotic bacterial strain, of the present invention is used with yoghurt production, such as fermented yoghurt drink, yoghurt, drinking yoghurt, cheese, fermented cream, milk based desserts and others. Suitably, the composition can be further used as an ingredient in one or more of cheese applications, meat applications, or applications comprising protective cultures.

In some embodiments, the food composition that comprises the bacterial strain, in particular the probiotic bacterial strain, of the present invention is suitable for preparing meal replacement product. As used herein, the term "meal replacement product" unless otherwise specified, includes any nutritional product containing protein, carbohydrate, lipid, vitamins and minerals, the combination of which is then suitable as a sole or primary nutrition source for a meal. Typically, the meal replacement product comprises at least one carbohydrate source, at least one lipid source and/or at least one protein source. As protein source, any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The proteins may be intact or hydrolyzed or a mixture of intact and hydrolyzed proteins. It may be desirable to supply partially hydrolyzed proteins (degree of hydrolysis between 2 and 20%), for example for animals believed to be at risk of developing cows' milk allergy. If hydrolyzed proteins are required, the hydrolysis process may be carried out as desired and as is known in the art. For example, a whey protein hydrolysate may be prepared by enzymatically hydrolyzing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil. The source of carbohydrates preferably provides 40% to 80% of the energy of the composition. Any suitable carbohydrate may be used, for example sucrose, lactose, glucose, fructose, corn syrup solids, maltodextrins, and mixtures thereof. Typically, substituting one daily meal by an energy restricted diet with a meal replacement contributes to the maintenance of weight after weight loss.

The food composition that comprises the bacterial strain, in particular the probiotic bacterial strain, of the present invention typically comprises carriers or vehicles. "Carriers" or "vehicles" mean materials suitable for administration and include any such material known in the art such as, for example, any liquid, gel, solvent, liquid diluent, solubilizer, or the like, which is non-toxic and which does not interact with any components, in particular with the bacterial strain, of the composition in a deleterious manner. Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In some embodiments, the food composition that comprises the bacterial strain, in particular the probiotic bacterial strain, of the present invention comprises an amount of dietary fibers. Dietary fiber passes through the small intestine undigested by enzymes and functions as a natural bulking agent and laxative. Dietary fiber may be soluble or insoluble and in general a blend of the two types is preferred. Suitable sources of dietary fiber include soy, pea, oat, pectin, guar gum, gum Arabic, fructooligosaccharides, galactooligosaccharides, sialyl-lactose and oligosaccharides derived from animal milks. In some embodiments, the dietary fiber is selected among mannans. Mannans (such as glucomannans and galactomannans), such as guar gum, locust bean gum, konjac, and xanthan gum, are present in some plant cell walls. The glucomannans are generally comprised of (1-4)-β-linked glucose and mannose units, while the galactomannans are generally comprised of a (1-4)-β-mannan backbone substituted with single units of (1-6)-α-galactose. Many endospermic legumes, such as guar and locust bean, contain galactomannans in the endosperm during seed development. Glucomannans have also been found as a minor component of cereal grains.

In some embodiments, the food composition that comprises the bacterial strain, in particular the probiotic bacterial strain, of the present invention contains minerals and micronutrients such as trace elements and vitamins in accordance with the recommendations of Government bodies such as the USRDA. For example, the composition may contain per daily dose one or more of the following micronutrients in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

In some embodiments, the composition that comprises the bacterial strain, in particular the probiotic bacterial strain, of the present invention contains emulsifiers. Examples of food grade emulsifiers typically include diacetyl tartaric acid esters of mono- and di-glycerides, lecithin and mono- and di-glycerides. Similarly, suitable salts and stabilizers may be included.

In some embodiments, the food composition that comprises the probiotic bacterial strain of the present invention contains at least one prebiotic. "Prebiotic" means food substances intended to promote the growth of the probiotic bacterial strain of the present invention in the intestines. The prebiotic may be selected from the group consisting of oligosaccharides and optionally contains fructose, galactose, mannose, soy and/or inulin; and/or dietary fibers.

In some embodiments, the composition that comprises the bacterial strain, in particular the probiotic bacterial strain, of the present invention contains protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. In all cases, such further components will be selected having regard to their suitability for the intended recipient.

The invention will now be described in more detail with reference to the following figures and examples.

SEQUENCES

SEQ ID NO: 1 shows the amino acid sequence of the chaperon protein ClpB from *E. coli* K12 referenced under NCBI Reference Number NP_417083.1 and referenced under Uni-Prot entry P63284.

SEQ ID NO: 2 shows amino acids 542 to 548 of the amino acid sequence of the chaperon protein ClpB from *E. coli* K12 of SEQ ID NO: 1.

SEQ ID NO: 3 shows the amino acid sequence of α-MSH from Homo sapiens referenced under Gen Pept Sequence ID, PRF: 223274.

SEQ ID NO: 4 shows the nucleic acid sequence of the nucleotide primers ClpB.

SEQ ID NO: 5 shows the nucleic acid sequence of the nucleotide primers ClpB.

FIGURES

FIGS. 1A-E: Proteomic identification of molecular mimicry between *E. coli* K12 proteins and α-MSH.

(a) 2D GE of *E. coli* cytoplasmic proteins. (b, c) Immunoblots of *E. coli* proteins detected with Rb anti-α-MSH IgG, preadsorbed (c) or not (b) with α-MSH. Circles in red surround the spots specifically recognized by α-MSH IgG which were used for protein identification. Circles in blue indicate nonspecific spots. Proteins identified in the spots 1-4 are isoforms of ClpB. (d) α-MSH and ClpB amino-acid sequence alignments using the Stretcher program. (e) Western blot of the recombinant ClpB, revealed with anti-α-MSH IgG. Lanes 1 and 2, 20 and 10 μg of ClpB, respectively.

FIGS. 2A-K. ClpB immunization in mice.

ClpB-immunized mice (ClpB+Adj) were compared with mice receiving adjuvant (Adj), PBS or controls (Ctr). (a) Body weight changes during 32 days of the study. Food intake and feeding pattern were studied during the last 2 weeks in the BioDAQ cages. Mean daily food intake (b), meal size (c) and meal number (d) during last 10 days of the study. (e) Food intake during 24 h after injection of α-MSH (100 μg kg-1 body weight, i.p.) or PBS. (f) Plasma levels of ClpB-reactive IgG before and after adsorption with $10^{-6}$M α-MSH. (g) Affinity of anti-ClpB IgG shown as the dissociation equilibrium constants (KD values). (h) Plasma levels of α-MSH-reactive total IgG. (i) Affinity (KD) of anti-α-MSH IgG. (j) cAMP assay in human embryonic kidney-293 cells overexpressing MC4R after stimulation by α-MSH alone or together with IgG (0.5 mg ml$^{-1}$) pooled from ClpB-immunized or from Adj-injected mice. (k) The cAMP assay was performed with IgG depleted from anti-α-MSH IgG. (a) Two-way repeated measurement analysis of variance (ANOVA) before α-MSH injection (100 μg kg$^{-1}$ body weight, i.p.), Po0.0001, Bonferroni post tests *a at least, Po0.05 ClpB group vs Ctr; *b at least, Po0.05 Adj group vs Ctr.; *c, Po0.05, Student's t-test ClpB group vs PBS; and *d, Po0.05, Student's t-test ClpB group vs Ctr. (b) ANOVA P=0.0002, Tukey's post tests *Po0.001, Po0.01, #Po0.05, Student's t-test. (c) ANOVA P=0.007, Tukey's post tests **Po0.01. (e) Student's t-test, *P00.05. (f, g) ANOVA Po0.0001, Tukey's posttests *Po0.001 ClpB+Adj vs other groups, paired t-test ##Po0.01, ###Po0.001. (h) ANOVA P=0.0002, Tukey's post tests *Po0.001, *P00.05; (i) Kruskal-Wallis test P=0.003, Dunn's post test **Po0.01, (mean±s.e.m., n=8). (j) ANOVA P=0.005, Tukey's post test *P00.05; ANOVA P=0.04, Student's t-test #Po0.05, aClpB vs α-MSH, bClpB vs Adj. (mean±s.e.m.; j, n=6, k, n=3).

FIG. 3A-J: *E. coli* supplementation in mice.

Effects of intragastric daily gavage (days 1-21) in mice with either *E. coli* K12 wild-type (WT), ClpBdeficient (ΔClpB) *E. coli* K12 or LB medium on body weight (a), food intake (b), meal size (c) and meal number (d). (e) PCR detection of a 180-base pair fragment of the bacterial ClpB DNA, first lane, molecular weight marker, second lane DNA from in vitro cultures of *E. coli* K12 WT, third lane DNA from in vitro cultures of *E. coli* K12 ΔClpB, and the remaining lanes DNA from mice feces collected at day 21. Plasma levels in optical density in enzyme-linked immunosorbent assay of anti-ClpB IgM (f) and IgG (g) before and after adsorption with $10^{-6}$M α-MSH.

Plasma levels of anti-α-MSH IgM (h) and IgG (i). a) Affinity (equilibrium constant) of anti-α-MSH IgG. (a) Two-way repeated measurements analysis of variance (ANOVA), P=0.3, Bonferroni post test day 2, **Po0.01 control (Ctr) vs *E. coli* WT. (b) ANOVA days 1-2, P=0.0006, Tukey's post tests ***Po0.001, *P00.05, *E. coli* WT vs aCtr and bLB. (c) Kruskal-Wallis (K-W) test third week P=0.0001, Dunn's post tests, *Po0.001, Po0.01, *E. coli* WT vs aCtr, bLB and CΔClpB. (d) ANOVA days 1-2, P=0.006, Tukey's post tests **Po0.01, *P00.05, K-W test third week Po0.0001, Dunn's post tests, *Po0.001, Po0.01, *E. coli* WT vs aCtr, bLB and CΔClpB. (f) K-W test, before adsorption P=0.02, Dunn's post tests *P00.05, ANOVA after adsorption, Po0.0001, Tukey's post tests **Po0.01, *E. coli* WT vs other groups. (g) ANOVA before adsorption, P=0.01, Tukey's post tests *P00.05, *E. coli* WT vs other groups, paired t-test ##Po0.01. (h) Student's t-test, *E. coli* WT vs other groups *P00.05. (j) K-W test P=0.02, Dunn's post test *P00.05, Mann-Whitney test, #Po0.05. (mean±s.e.m., n=8).

FIG. 4A-F. Anti-ClpB antibodies in ED patients.

Plasma levels of anti-ClpB IgG (a) and IgM (b) in healthy women (control, Ctr) and in patients with AN, BN and BED. Plasma levels of ClpB IgG (c) and IgM (d) before and after adsorption with $10^{-6}$M α-MSH. Percentage of α-MSH crossreactive anti-ClpB IgG (e) and IgM (f). (b) Student's t-test *Po0.05. (c, d) Paired t-tests, *Po0.001, Po0.01. (e) Kruskal-Wallis test Po0.0001, Dunn's post test, **Po0.01, Mann-Whitney test #Po0.05. (f) Analysis of variance P=0.02, Tukey's post test *P00.05. (mean±s.e.m., Ctr, n=65, AN, n=27 BN, n=32 and BED, n=14).

Figure 5:
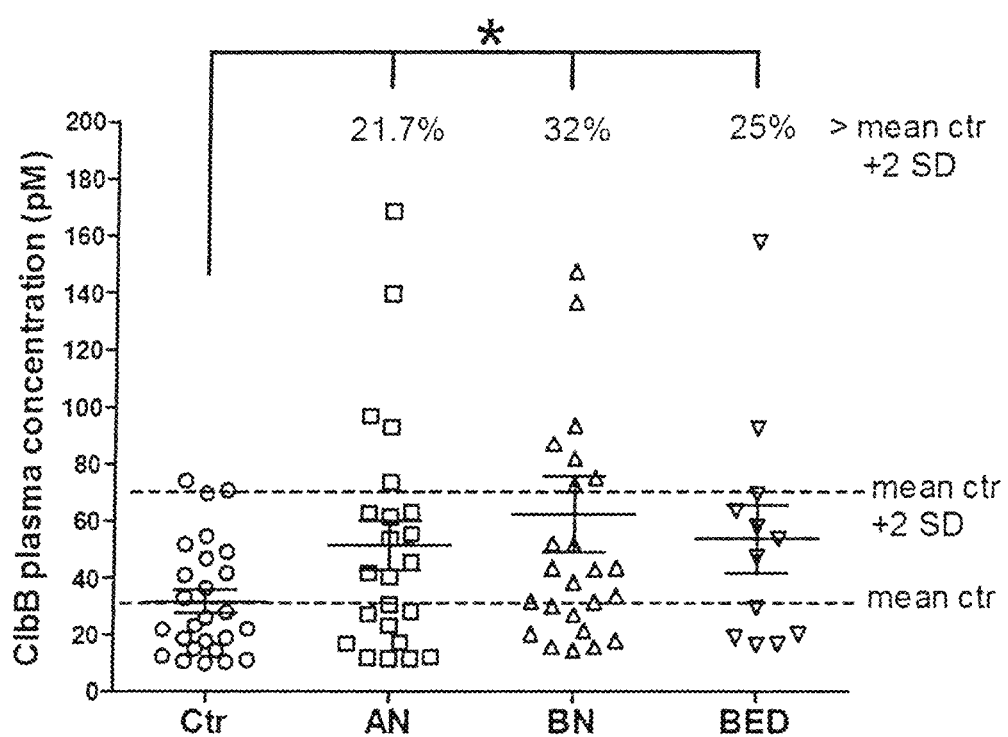

FIG. 5. Plasma concentrations of bacterial ClpB protein in patients with eating disorders and healthy controls (Ctr).

AN, anorexia nervosa, BN, bulimia nervosa, BED, binge-eating disorder. *p<0.05 Student's t-test of mean ClpB concentrations vs. Ctr. Percentage (%) of patients having ClpB concentrations higher than mean+2 standard deviations (SD) of controls.

Figure 6:
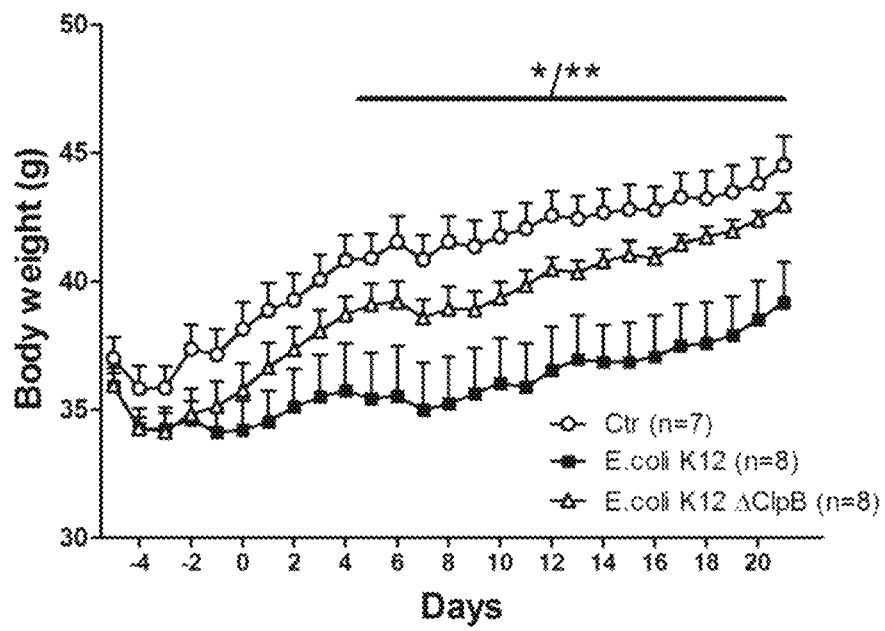

FIG. 6: Body weight dynamics in obese ob/ob mice before and during (Days 0-21) intragastric gavage with *E. coli* K12, *E. coli* K12 ΔClpB, both in Mueller-Hilton (MH) medium, or with MH medium only, as a control (Ctr). 2-way ANOVA, Effect of treatment: p=0.01, Bonferroni post-tests Ctr. vs. *E. coli* K12, * p<0.05 and **p<0.01. Mean±SEM.

Figure 7:
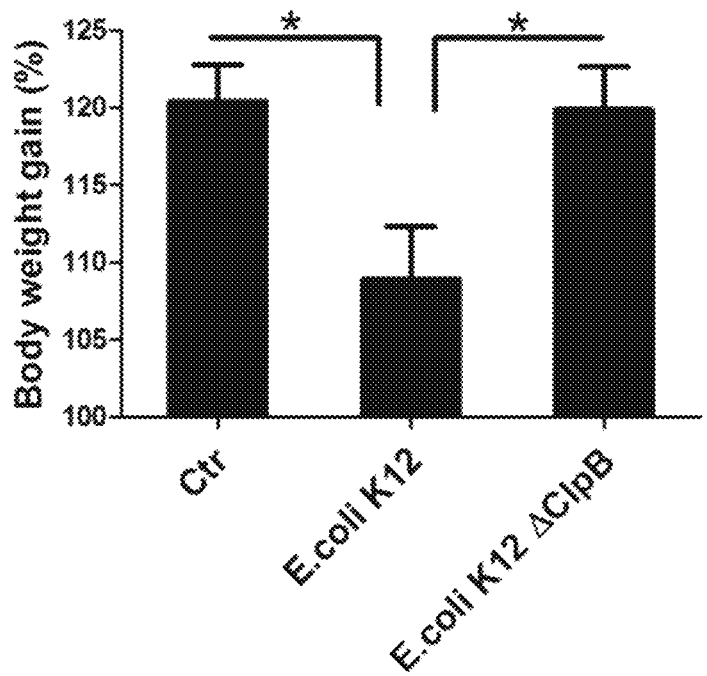

FIG. 7: Percentage of mean body weight change (from the day of randomization=100%) in obese ob/ob mice after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.01, Tukey's post-tests * p<0.05. Mean±SEM.

Figure 8:
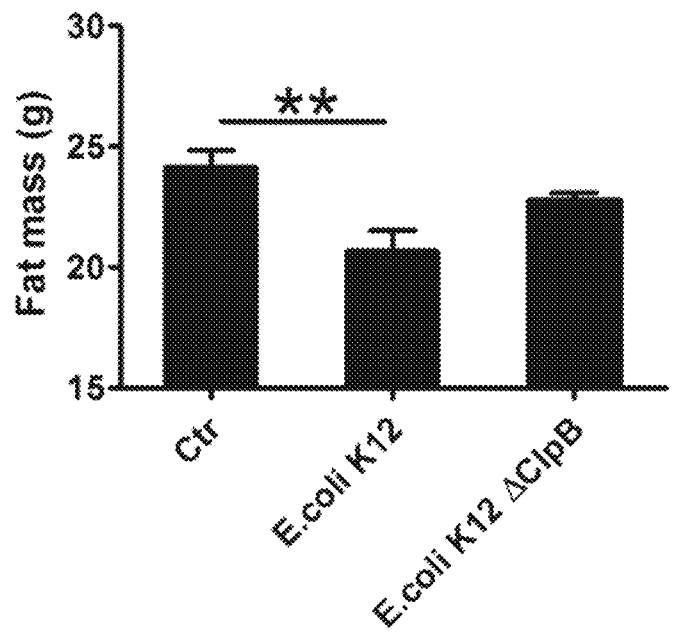

FIG. 8: Fat content in obese ob/ob mice measured by EchoMRI after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.005, Tukey's post-test **p<0.01. Mean±SEM.

Figure 9:
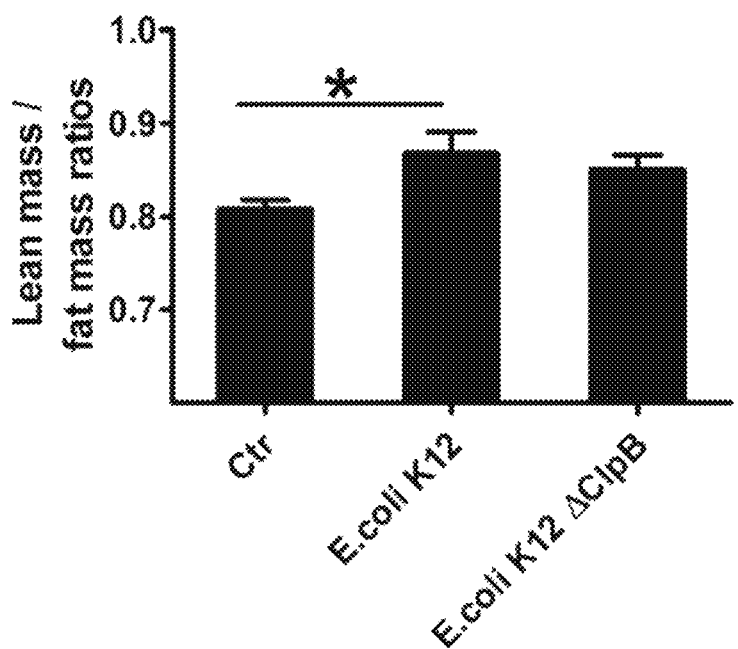

FIG. 9: Lean to fat mass ratios in obese ob/ob mice measured by EchoMRI after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.05, Student's t-test *p<0.05. Mean±SEM.

Figure 10:
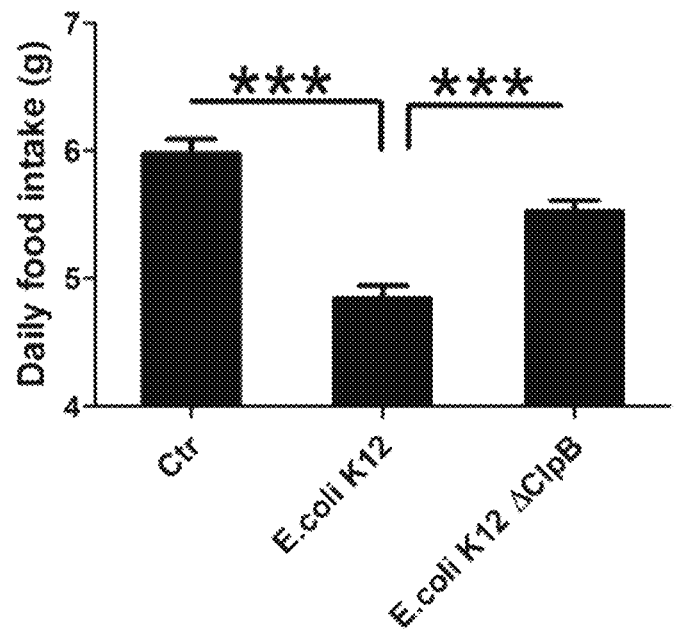

FIG. 10: Mean daily food intake in obese ob/ob mice during 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p<0.0001, Tukey's post-test ***p<0.001. Mean±SEM.

Figure 11:
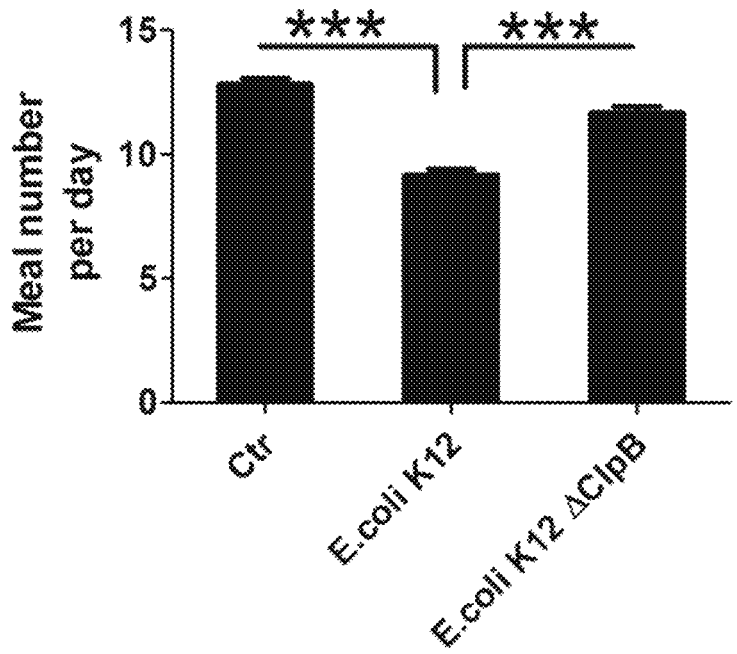

FIG. 11: Mean daily meal number in obese ob/ob mice during 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p<0.0001, Tukey's post-test ***p<0.001. Mean±SEM.

Figure 12:
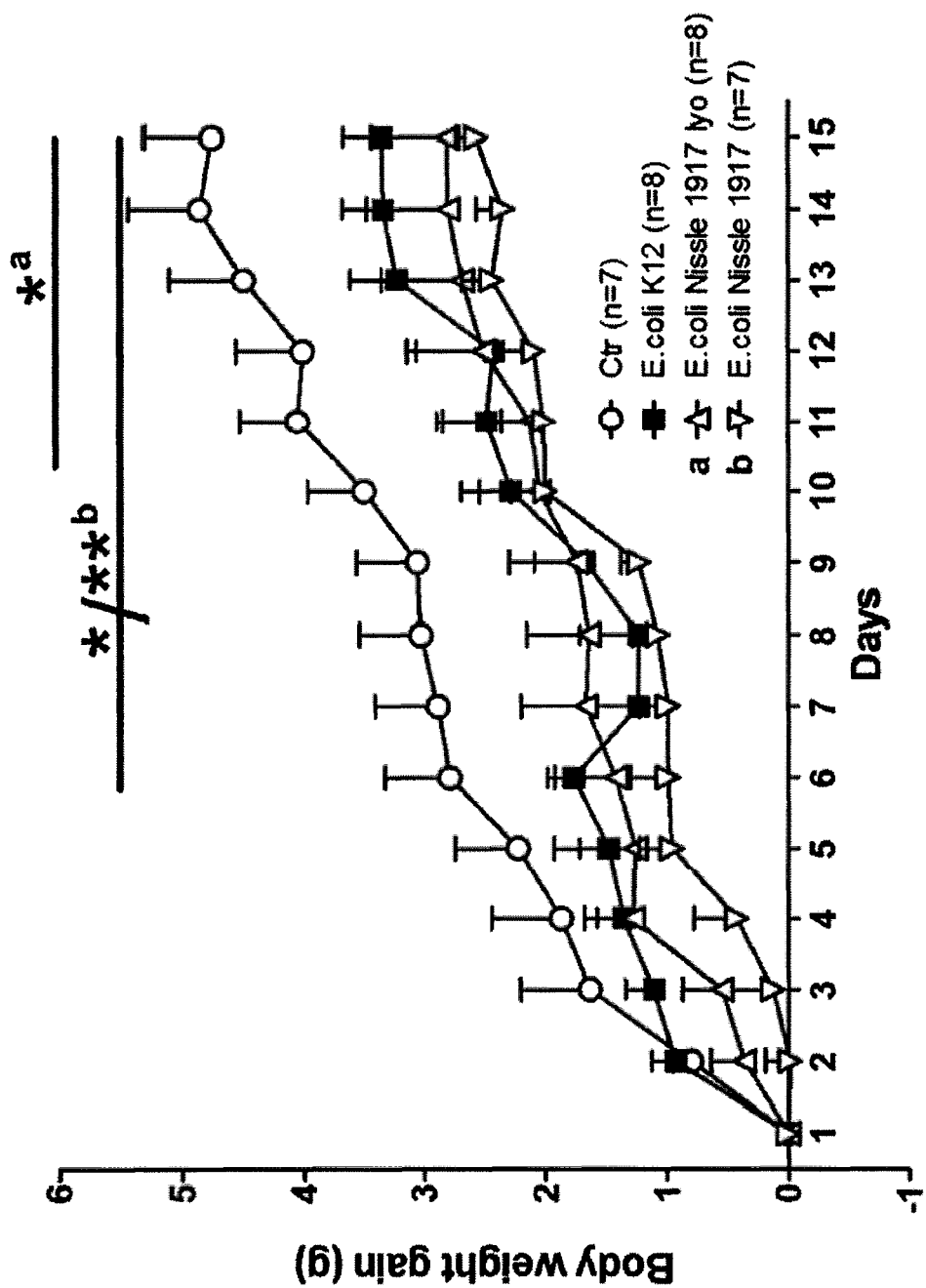

FIG. 12: Daily body weight gain in obese ob/ob mice during intragastric gavage with *E. coli* K12, *E. coli* Niessle 1917, *E. coli* Niessle 1917 lyophilized (lyo), all in Mueller-Hilton (MH) medium, or with MH medium only, as a control (Ctr). 2-way ANOVA, p=0.02, Bonferroni post-tests a, Ctr. vs. *E. coli* Niessle 1917 lyo and b, Ctr. vs. *E. coli* Niessle 1917, * p<0.05 and **p<0.01. Mean±SEM.

Figure 13:
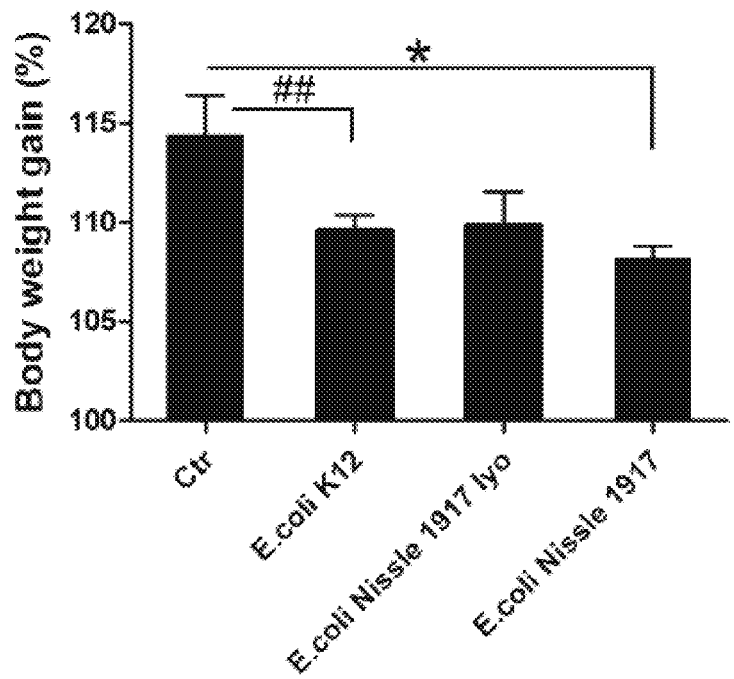

FIG. 13: Percentage of mean body weight change (from the day of randomization=100%) in obese ob/ob mice after 2 weeks of intragastric gavage with *E. coli* K12, *E. coli* Niessle 1917, *E. coli* Niessle 1917 lyophilized (lyo), all in Mueller-Hilton (MH) medium, or with MH medium only, as a control (Ctr). Kruskal-Wallis p<0.01, Dunn's post-test *p<0.05, Mann-Whitney test ##p<0.01. Mean±SEM.

Figure 14:
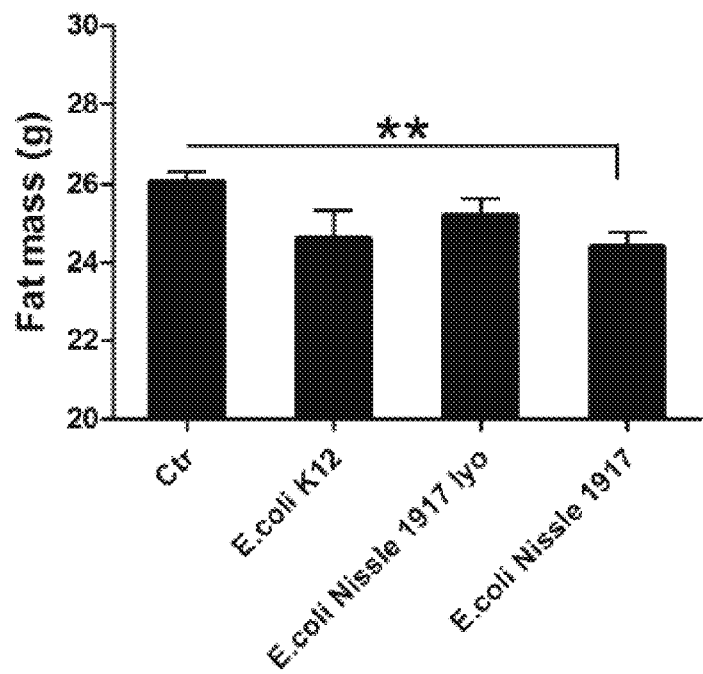

FIG. 14: Fat content in obese ob/ob mice measured by EchoMRI after 2 weeks of intragastric gavage with *E. coli* K12, *E. coli* Niessle 1917, *E. coli* Niessle 1917 lyophilized (lyo), all in Mueller-Hilton (MH) medium, or with MH medium only, as a control (Ctr). Student's t-test **p<0.01. Mean±SEM.

Figure 15:
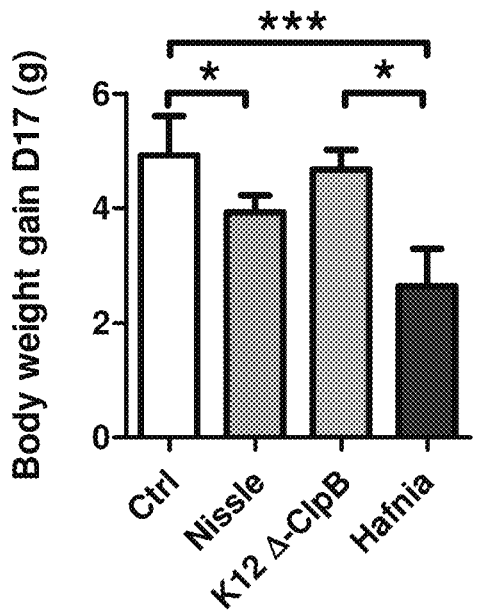

FIG. 15: Body weight gain (in g) in obese ob/ob mice after 17 days of intragastric gavage with *E. coli* Niessle 1917 (Nissle) (n=15), *E. coli* K12 (K12 Δ-ClpB) (n=15) or *Hafnia alvei* AF036 (*Hafnia*) (n=15), all in Mueller-Hilton (MH) medium, or with MH medium only, as a control (Ctrl) (n=12).

Figure 16:
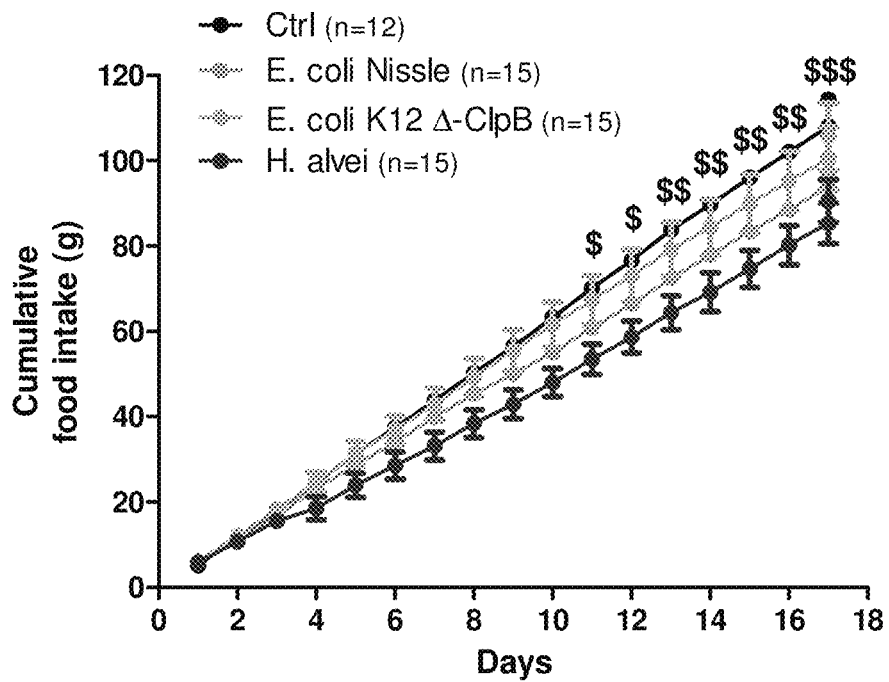

FIG. 16: Cumulative food intake (in g) in obese ob/ob mice after 17 days of intragastric gavage with *E. coli* Niessle 1917 (Nissle) (n=15), *E. coli* K12 (K12 Δ-ClpB) (n=15) or *Hafnia alvei* AF036 (*Hafnia*) (n=15), all in Mueller-Hilton (MH) medium, or with MH medium only, as a control (Ctrl) (n=12).

Figure 17A:
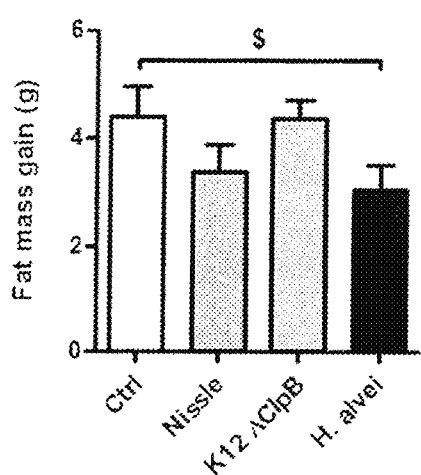
Figure 17B:
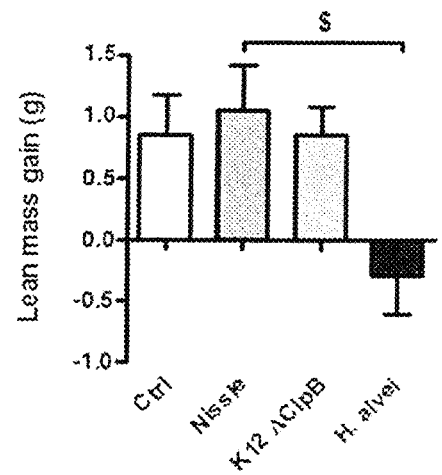
Figure 17C:
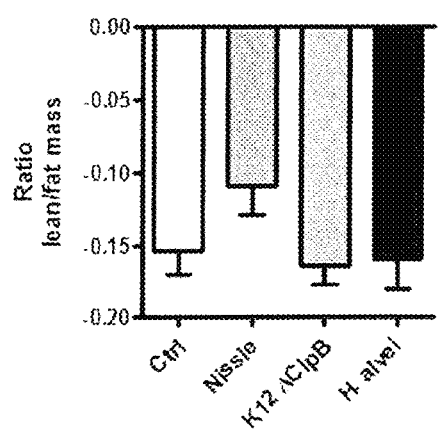

FIGS. 17A-C: Fat and lean mass gain in obese ob/ob mice measured by EchoMRI after 17 days of intragastric gavage with *E. coli* Niessle 1917 (Nissle) (n=15), *E. coli* K12 (K12 ΔClpB) (n=15) or *Hafnia alvei* AF036 (*H. alveri*) (n=15), all in Mueller-Hilton (MH) medium, or with MH medium only, as a control (Ctrl) (n=12). A. Fat mass gain (in g). B. Lean mass gain (in g). C. Lean-to-fat mass ratios.

Figure 18A:
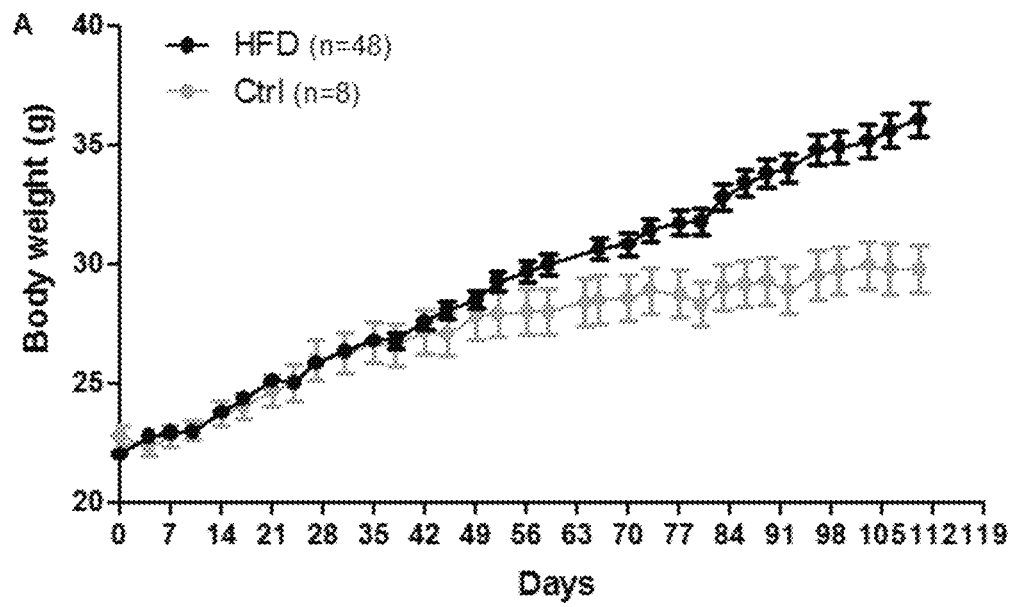
Figure 18B:
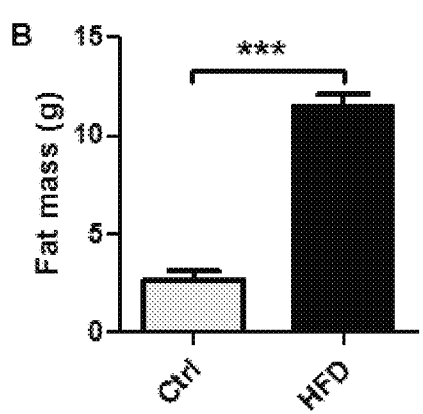
Figure 18C:
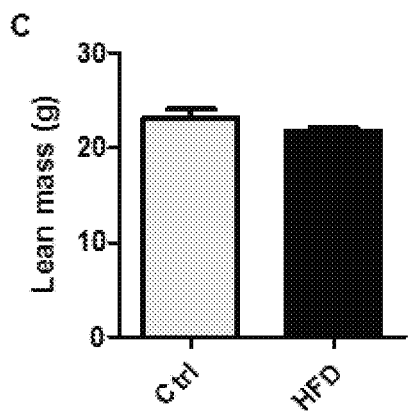

FIGS. 18A-C: High fat diet validation. A. Body weight (in g) in mice fed with a high fat/high carbs diet (HFD) (n=48) and in mice fed with a control diet (Ctrl) (n=8). B. Fat mass (in g). C. Lean mass (in g).

Figure 19:
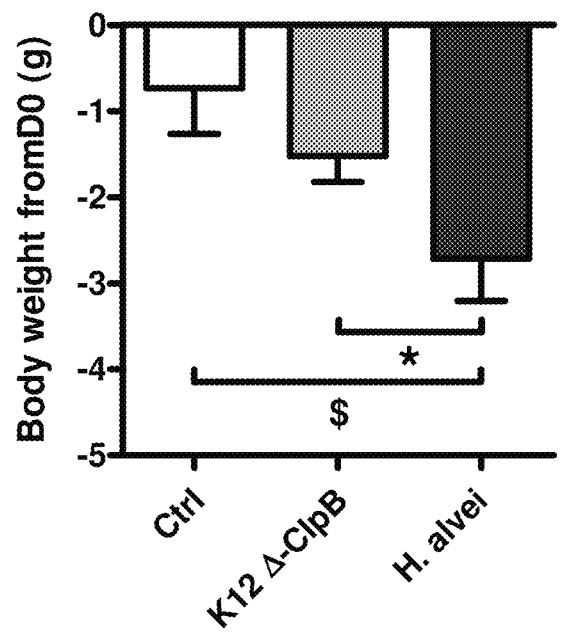

FIG. 19: Reduction in body weight gain from D0 in high fat diet (HFD)-induced obese mice after 14 days of intragastric gavage with *E. coli* K12 (K12 Δ-ClpB) or *Hafnia alvei* AF036 (*H. alvei*), all in Mueller-Hilton (MH) medium, or with MH medium only, as a control (Ctrl).

Figure 20A:
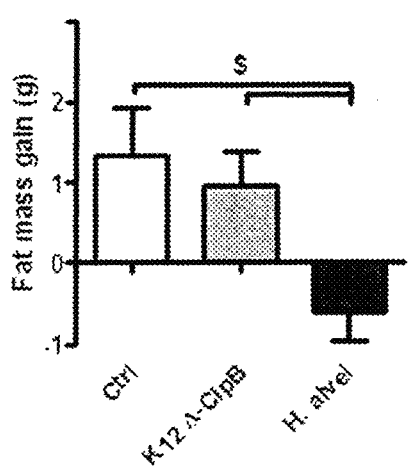
Figure 20B:
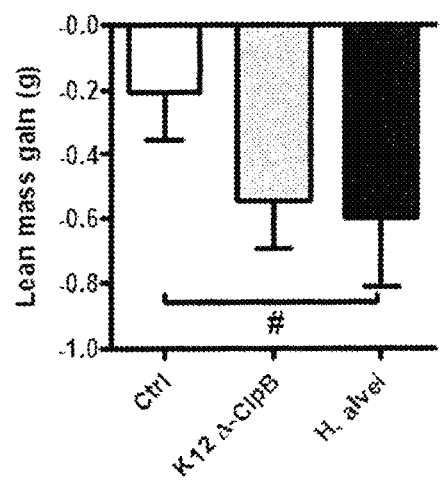

FIGS. 20A-B: Fat and lean mass gain from D0 in high fat diet (HFD)-induced obese mice after 14 days of intragastric gavage with *E. coli* K12 (K12 Δ-ClpB) or *Hafnia alvei* AF036 (*H. alvei*), all in Mueller-Hilton (MH) medium, or with MH medium only, as a control (Ctrl). A. Fat mass gain (in g). B. Lean mass gain (in g).

Figure 21:
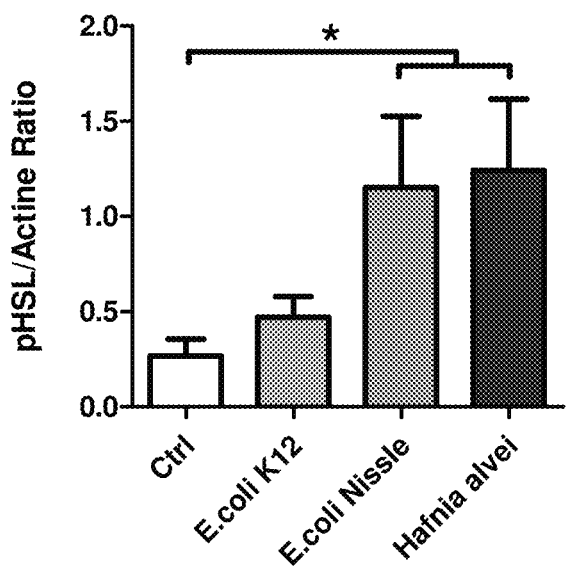

FIG. 21: Relative hormone-sensitive lipase protein (pHSL) expression rate (against actin expression rate as a standard) in obese ob/ob mice after 17 days of intragastric gavage with *E. coli* Niessle 1917 (*E. coli* Nissle) (n=15), *E. coli* K12 (*E. coli* K12) (n=15) or *Hafnia alvei* AF036 (*Hafnia alvei*) (n=15), all in Mueller-Hilton (MH) medium, or with MH medium only, as a control (Ctrl) (n=12). HSL and actine expression rates were measured by western blot.

Figure 22:
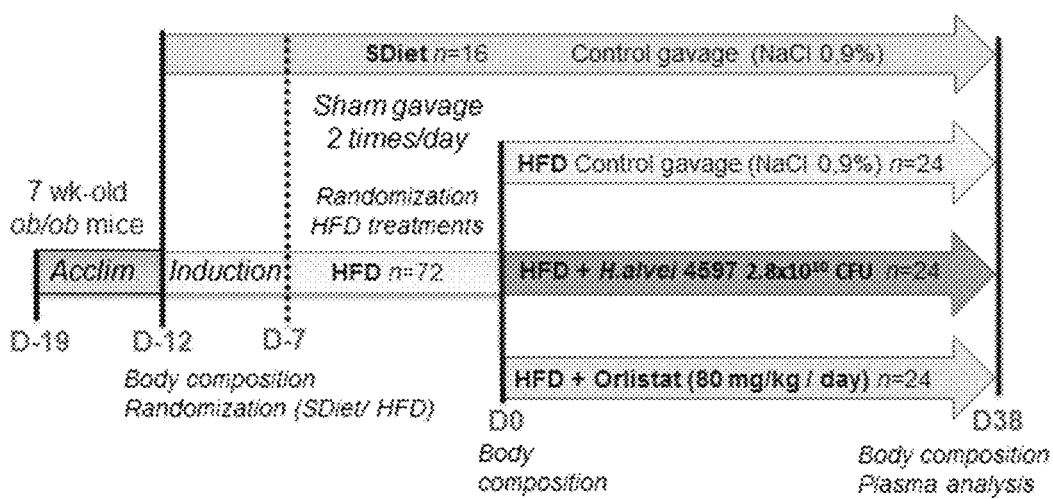

FIG. 22: Experimental protocol of the study of examples 7-10.

FIGS. 23A-C: Effects of *H. alvei* and orlistat on body weight in high-fat-diet (HFD)-fed ob/ob mice as compared to standard diet (SDiet). (A) Body weight dynamics, vertical dashed line defines beginning of *H. alvei* or orlistat treatments (B) Body weight gain dynamics. (C) Body weight gain during treatment as an area under curve (AUC). (A,B) Two-way RM ANOVA, p<0.0001, Bonferroni's posttests, HFD vs. HFD+Orlistat, * p<0.001,  p<0.01, * p<0.05; C. ANOVA, p<0.0001, Tukey's posttests ays. HFD and bvs. HFD+*H. alvei*, both *** p<0.001, Student's Nests, * p<0.05, (mean±SEM; SDiet, n=16, all other groups, n=24).

FIGS. 24A-C: Effects of *H. alvei* and orlistat on body composition in high-fat-diet (HFD)-fed ob/ob mice as compared to standard diet (SDiet). Percentage of fat (A) and lean (B) mass, as well as lean/fat mass ratio (C) at the end of the treatment. (A,C) ANOVA, p=0.0004, (B) ANOVA, p=0.0002, Bonferroni's posttests, *** p<0.001, * p<0.05. (A-C) Student's Nests, #p<0.05, (mean±SEM; SDiet, n=16, all other groups, n=24).

FIGS. 25A-C: Effects of *H. alvei* and orlistat on food intake in high-fat-diet (HFD)-fed ob/ob mice as compared to standard diet (SDiet). (A) Dynamics of daily food intake. (B) Dynamics of cumulative food intake/mouse. (C) Mean cumulative food intake/mouse. (A) Two-way RM ANOVA, p<0.0001, Bonferroni's posttests, HFD vs. HFD+Orlistat. *** p<0.001, * p<0.05 days 8, 9, 14 and 19. HFD+*H. alvei* vs. HFD+Orlistat. *** p<0.001, * p<0.05 days 5 and 6. (B) Two-way RM ANOVA, p<0.0001, Bonferroni's posttests, HFD vs. HFD+Orlistat. * p<0.001;  p<0.01 days 24, 25; * p<0.05 days 22,23. HFD+*H. alvei* vs. HFD+Orlistat. * p<0.001,  p<0.01, days 17, 18; * p<0.05 days 15,16. (C). ANOVA p<0.0001, Tukey's posttests *** p<0.001, * p<0.05, (mean±SEM; SDiet, n=16, all other groups, n=24).

FIGS. 26A-E: Effects of *H. alvei* HA4597™ and orlistat on glycemia and obesity-related metabolic parameters in high-fat-diet (HFD)-fed ob/ob mice as compared to standard diet (SDiet). (A) Plasma glucose levels in ad libitum feeding conditions. (B) OGTT after overnight fasting. Plasma levels of (C) triglycerides, (D) total cholesterol, and (E) alanine aminotransferase (ALAT) in ad libitum feeding conditions. (A). ANOVA p<0.05, Tukey's posttest vs. SDiet * p<0.05. Student's t-test #p<0.05. (B) Two-way RM ANOVA p<0.05, Bonferroni posttests, SDiet vs. HFD+orlistat * p<0.05 and a* p<0.05, ** p<0.01 for 90 and 120 min; HFD+*H. alvei* vs. HFD+Orlistat b* p<0.05, ** p<0.01 for 90 min. (C) ANOVA p<0.05, Tukey's posttest vs. SDiet * p<0.05. (D) ANOVA p<0.001, Tukey's posttests * p<0.001,  p<0.01, Student's t-test #p<0.05. (E) ANOVA p=0.0006, Tukey's posttests ** p<0.01, * p<0.05, (mean±SEM; SDiet, n=8, all other groups n=12).

EXAMPLES

The following examples demonstrate that the ClpB chaperon protein of commensal gut bacteria *E. coli* K12 is a conformational mimetic of α-melanocyte-stimulating hormone (α-MSH), a neuropeptide involved in the regulation of energy metabolism and emotion. They also reveal a molecular link between ClpB expressing gut bacteria and the regulation of motivated behavior and emotion via production of ClpB protein and anti-ClpB antibodies crossreactive with α-MSH. They further support the involvement of ClpB-expressing microorganisms in increased ClpB protein and ClpB antibody production and establishment of abnormal feeding behavior and emotion.

Example 1

Materials and Methods

E. coli K12 Culture and Protein Extraction

The bacterial strain used in this study was E. coli K12, provided by UMR 6270 CNRS Laboratory in Rouen University, France. E. coli K12 was grown in 250 ml Luria Bertani (LB) broth (MP Biomedicals, Illkirch, France) at 37° C. for 24 h. Protein extraction was performed as described by Marti et al. (PLoS ONE 2011, e26030). In brief, bacteria were harvested by centrifugation at 4000 g for 30 min at 4° C. and the resulting pellet was resuspended in extraction buffer (300 mM NaCl and 20 mM Tris-HCl, pH 8). The suspension was disrupted by sonication (3×3 min, pulse ON 1 s, OFF 1 s at 21% of amplitude) and centrifuged at 10 000 g for 10 min at 4° C. The supernatant was recovered and ultracentrifuged at 4° C. for 45 min at 60 000 g to further separate proteins into cytoplasmic (supernatant) and envelope (pellet) fractions. Protein concentrations were measured using 2-D Quant Kit (GE Healthcare, Piscataway, N.J., USA).

Two-Dimensional Polyacrylamide Gel Electrophoresis

For two-dimensional (2D) polyacrylamide gel electrophoresis (PAGE), 400 μg of E. coli K12 protein extract were added to iso-electro focusing buffer (7M urea, 2M thiourea and 0.5% ampholytes, pH 4-7, 20 mM DTT, 2 mM TBP, 2% CHAPS and 0.005% bromophenol blue) and solubilized for 60 min at room temperature with slight shaking. The first-dimensional gel separation was carried out using ReadyStrip IPG Strip (18 cm, pH 4-7 NL, Bio-Rad, Marnes-la-Coquette, France). After 24 h of passive rehydration of the strip with iso-electro focusing buffer, the protein sample was added to the strips through a loading cup placed at 1.5 cm from the cathode. Isoelectro focusing was performed with the Ettan IPGphor 3 System (GE Healthcare, Orsay, France) in four steps (31 500 Vh): 500 V for 1 h, 1000 V gradient, 10 000 V gradient and 10 000 V for 2 h. After two equilibration steps with 2% DTT and 2.5% iodoacetamide, respectively, the second dimension, that is, a SDS-PAGE, (10% polyacrylamide gel, 20 cm×18-cm×1 mm) was performed on an Ettan Daltsix vertical electrophoresis system (GE Healthcare) with 12 mA per gel. After SDS-PAGE, the 2D gel was fixed for 2 h in 2% (vol:vol) orthophosphoric acid and in 50% (vol:vol) methanol at room temperature. Gels were then rinsed with water, and the protein spots were visualized by CBB G-250 (Bio-Rad) staining (34% (vol:vol) methanol, 17% (wt:vol) ammonium sulfate, 2% (vol:vol) orthophosphoric acid and 0.66 g CBB G-250 per liter).

Immunoblotting

Following 2D-PAGE, E. coli cytoplasmic proteins were transferred onto Hybond-ECL PVDF membrane (GE Healthcare) via a dry transfer method (Trans Blot Cell, Bio-Rad, USA) and a constant current of 0.8 mA.cm$^{-2}$ of the membrane size for 2 h. After transfer, membranes were blocked with 5% (wt:vol) milk (Regilait, France) in phosphate-buffered saline (PBS; 10 mmol·l$^{-1}$ Tris, pH 8, and 150 mM·l$^{-1}$ NaCl) plus 0.05% (vol:vol) Tween 20. After washes, membranes were incubated overnight at 4° C. with polyclonal rabbit anti-α-MSH IgG (1:1000, Peninsula Laboratories, San Carlos, Calif., USA), followed by washes and incubation with polyclonal swine anti-rabbit horseradish peroxidase-conjugated Igs (1:3000; Dako, Trappes, France). Immunoblots were revealed by the ECL detection system (GE Healthcare) and were scanned with ImageScanner 11 (GE Healthcare) previously calibrated by using a greyscale marker (Kodak) and digitalized with Labscan 6.00 software (GE Healthcare). The same procedure was performed after adsorption of rabbit anti-α-MSH IgG with 10$^{-6}$M of α-MSH peptide (Bachem AG, Bubendorf, Switzerland) overnight at 4° C.

Protein Identification

The protein spots of interest were excised from CBB G-250-stained 2D gels using the Ettan Spot Picker (GE Healthcare), and automated in-gel digestion of proteins was performed on the Ettan Digester (GE Healthcare). Protein extracts were then resuspended in 10 μl of 5% (vol:vol) acetonitrile/0.1% (vol:vol) formic acid and then analyzed with a nano-LC1200 system coupled to a 6340 Ion Trap mass spectrometer equipped with a nanospray source and an HPLC-chip cube interface (Agilent Technologies, Courtaboeuf, France). In brief, peptides were enriched and desalted on a 40-nl RPC18 trap column and separated on a Zorbax (30-nm pore size, 5-μm particle size) C18 column (43 mm long×75 μm inner diameter; Agilent Technologies). A 9-min linear gradient (3-80% acetonitrile in 0.1% formic acid) at a flow rate of 400 nl·min$^{-1}$ was used, and the eluent was analyzed with an Ion Trap mass spectrometer. For protein identification, MS/MS peak lists were extracted and compared with the protein databases by using the MASCOT Daemon version 2.2.2 (Matrix Science) search engine. The searches were performed with the following specific parameters: enzyme specificity, trypsin; one missed cleavage permitted; no fixed modifications; variable modifications, methionine oxidation, cysteine carbamidomethylation, serine, tyrosine and threonine phosphorylation; monoisotopic; peptide charge, 2+ and 3+; mass tolerance for precursor ions, 1.5 Da; mass tolerance for fragmentations, 0.6 Da; ESI-TRAP as instrument; taxonomy, E. coli; National Center for Biotechnology Information (NCBI) database (NCBInr 20120531 (18280215 sequences, 6265275233 residues); Bethesda, Md., USA). Protein hits were automatically validated if they satisfied one of the following criteria: identification with at least two top-ranking peptides (bold and red) each with a MASCOT score of 454 (Po0.01), or at least two top-ranking peptides each with a MASCOT score of 447 (Po0.05). To evaluate false-positive rates, all the initial database searches were performed using the 'decoy' option of MASCOT. Results were considered relevant if the false-positive rate never exceeded 1%.

Protein Identification from OFFGEL

High-resolution E. coli K12 protein separation into 24 fractions was done onto the 3100 OFFGEL fractionator using the OFFGEL pH3-10 kit (Agilent Technologies). Protein samples (400 μg) preparation and assembly of all parts of the OFFGEL systems were done according to the procedures described in the Agilent Quick start Guide. OFFGEL fractionation was performed using the standard program OG24PRO with maximum limited current parameters (8000 V, 50 μA and 200 mW) until 64 KVh was reached after 30 h. At the end of the experiment, all fractions were transferred into a 0.8-ml deep well (Thermo Fisher Scientific, Illkirch, France) and stored at −20° C. Nine protein-containing fractions recovered from the central part of the OFFGEL were studied by western blot using rabbit anti-α-MSH IgG (Peninsula Laboratories) followed by protein identification as described above.

Immunization and Behavior in Mice

All experimental protocols were conducted according to US National Institutes of Health guidelines and EU directives, and animal experiments were approved by the Institutional Ethical Committees. Two-month-old male C57Bl6 mice (Janvier Laboratories, L'Arbresle, France) were acclimated to the animal facility for 1 week with 12 h light-dark cycle, lights on at 0700 hours and were kept in standard mouse-holding cages (n=8) each. Mice were fed ad libitum with standard pelleted rodent chow (RM1 diet, SDS, UK) with drinking water always available and were manipulated daily by gentle holding and measuring body weight. During acclimatization, mice were distributed between four cages to obtain the similar mean body weight per mouse per cage. After 1 week of acclimatization, mice from each cage were assigned to one of four study group and received following treatments: (i) Group 1, ClpB immunization (n=8): ClpB protein (Delphi Genetics, Gosselies, Belgium) 50 µg per mouse in 200 µl of 1:1 (vol:vol) of PBS with Complete Freund's Adjuvant (Sigma, St Louis, Mo., USA), intraperitoneally (i.p.); (ii) Group 2, adjuvant injection controls (n=8): 200 µl of Complete Freund's Adjuvant in PBS (1:1 (vol:vol), i.p.); (iii) Group 3, PBS injection controls (n=8): 200 µl of PBS (i.p.); and (iv) Group 4, intact controls (n=8): received no injections, and then all mice were returned to their holding cages. Fifteen days later, mice were given a boost immunization and the following treatments: (i) Group 1 (n=8), ClpB protein (Delphi Genetics) 50 µg per mouse in 200 µl of 1:1 (vol:vol) of PBS with Incomplete Freund's Adjuvant (Sigma) i.p.; (ii) Group 2 (n=8): 200 µl of Incomplete Freund's Adjuvant in PBS (1:1 (vol:vol), i.p.); (iii) Group 3, (n=8): 200 µl of PBS (i.p.); and iv) Group 4, (n=8): received no injections. Next day after the boost, mice were placed individually into the BioDAQ mouse cages (Research Diets, Inc., New Brunswick, N.J., USA) each equipped with an automatic feeding monitor. Food (Serlab, Montataire France) and drinking water were available ad libitum and body weight was measured daily. After 3 days of acclimatization to the BioDAQ cages, mice received the following treatments: Groups 1, 2 and 3 (each n=8), that is, mice that have been immunized with ClpB, injected with adjuvants and with PBS, respectively, all received an acute injection of α-MSH peptide (Bachem AG), 100 µg·kg$^{-1}$ body weight in 100 µl of PBS (i.p.) at 1000 hours. The control mice (n=8) received PBS only (i.p.). Feeding data was continuously monitored and analyzed using the BioDAQ data viewer 2.3.07 (Research Diets). For the meal pattern analysis, the inter-meal interval was set at 300 s. After the feeding study, mice were placed in individual mouse-holding cages with food and water available ad libitum, and were analyzed for locomotor activity and anxiety in 0-maze (Med Associate, Inc., St Albans, Vt., USA) tests performed during 2 consecutive days. Two hours after the 0-maze test, mice were killed by decapitation in a guillotine and trunk blood was collected into EDTA-containing tubes. Plasma was separated by centrifugation at 3500 r.p.m. (1.4 g) for 10 min at 4° C. and stored at −80° C. before assay.

Locomotor Activity and Anxiety Tests

After feeding study in the BioDAQ cages, mice were analyzed for locomotor activity using a Versamax Animal Activity Monitor (AccuScan Instruments, Inc., Columbus, Ohio, USA). Next day after the locomotor activity test, all mice were tested for their anxiety in an elevated O-maze. The elevated-O-maze is a variation of more commonly used elevated plusmaze pharmacologically validated for anxiety testing in rodents. The advantage of the O-maze is that it lacks the ambiguous central square of the traditional plusmaze. The O-maze consisted of a circular infrared platform (outer diameter 120 cm) elevated 80 cm above the floor, featuring two open and two closed segments made of gray plastic. The closed segments were enclosed by walls extending 20 cm above the surface of the maze and covered with a black infrared plexiglas lid. Each test started by placing the mouse into one of the two closed segments. The test lasted 5 min and was recorded using a video camera placed above the O-maze and the EthoVision video tracking software (Noldus IT, Wageningen, The Netherlands). Measurements of distance and time spent in the open and closed segments were analyzed. Between each mouse tests, the O-maze was cleaned with 30% ethanol.

ClpB and α-MSH Autoantibody Assay

Plasma levels of auto-Abs reacting with ClpB, α-MSH and adrenocorticotropic hormone were measured using enzyme-linked immunosorbent assay according to a published protocol (Fetissov S O., Methods Biol Mol 2011). In brief, ClpB protein (Delphi Genetics), α-MSH or adrenocorticotropic hormone peptides (Bachem AG) were coated onto 96-well Maxisorp plates (Nunc, Rochester, N.Y., USA) using 100 µl and a concentration of 2 µg·ml$^{-1}$ in 100 mM NaHCO3 buffer, pH 9.6, for 72 h at 4° C. Plates were washed (5 min for three times) in PBS with 0.05% Tween 200, pH 7.4, and then incubated overnight at 4° C. with 100 µl of mouse plasma diluted 1:200 in PBS to determine free auto-Ab levels or diluted 1:200 in dissociative 3M NaCl and 1.5M glycine buffer, pH 8.9, to determine total auto-Ab levels. The plates were washed (three times) and incubated with 100 µl of alkaline phosphatase (AP)-conjugated goat antimouse IgG (1:2000) or anti-mouse IgM (1:1000), all obtained from Jackson ImmunoResearch Laboratories, Inc. (West Grove, Pa., USA). Following washing (three times), 100 µl of p-nitrophenyl phosphate solution (Sigma) was added as AP substrate. After 40 min of incubation at room temperature, the reaction was stopped by adding 3 N NaOH. The optical density was determined at 405 nm using a microplate reader Metertech 960 (Metertech Inc., Taipei, Taiwan). Blank optical density values resulting from the reading of plates without addition of plasma samples were subtracted from the sample optical density values. Each determination was done in duplicate. The variation between duplicate values was inferior to 5%. Similar protocol was used to measure anti-ClpB IgG and IgM in human plasma (1:400) using corresponding anti-human IgG or IgM AP-conjugated antibodies (1:2000, Jackson ImmunoResearch Laboratories, Inc.).

Absorptions of ClpB Antibodies with α-MSH

Plasma samples of mice, diluted 1:200 in PBS, or humans, diluted 1:400 in PBS, were preincubated with 10$^{-6}$M α-MSH peptide (Bachem AG) overnight at 4° C. before adding the samples to 96-well Maxisorp plates (Nunc) coated with ClpB protein (Delphi Genetics). IgG and IgM antibodies reactive with ClpB were detected by enzyme-linked immunosorbent assay using corresponding anti-mouse or anti-human AP-conjugated antibodies (Jackson ImmunoResearch Laboratories, Inc.) as described above. Percentage of ClpB antibodies crossreactive with α-MSH were calculated relative to levels of anti-ClpB antibodies detected without absorption in each individual plasma sample equal 100%.

IgG Purification from Plasma

IgG purification and affinity assay were performed according to a published protocol (Legrand et al., Protoc Exch 2014, doi:10.1038/protex2014.004). Extraction of plasma globulins was done by plasma acidification and separation on C18 SEP column (Phoenix Pharmaceuticals, Burlingame, Calif., USA), then 500 µl of mouse plasma was mixed with 500 µl of buffer A (1% trifluoroacetic acid in water). The column was activated in 1 ml of buffer B (60% acetonitrile in 1% trifluoroacetic acid) by 3 min centrifugation with 700 r.p.m. and rinsed three times with 3 ml of buffer A. Diluted plasma (1:1 in buffer A) was added to the column and the effluent (1 ml) was saved (frozen at −20° C.) for further purification of IgG. Total IgG were purified from the effluents of mouse plasma samples using the Melon Gel Kit (Thermo Fisher Scientific, Rockford, Ill., USA). Plasma effluents diluted 1:4 in kit's purification buffer was added on washed melon gel deposited in a column. Column was spun 1 min at 6000 r.p.m., and the IgG containing effluent was saved and frozen at −20° C. before lyophilization. Lyophilized IgG were reconstituted in the HBS-EP buffer (GE Healthcare, Piscataway, N.J., USA). For the cyclic adenosine monophosphate (cAMP) experiment, IgG purified from eight mice of the ClpB and of the adjuvant control group were combined, respectively, into two pools that were divided in two parts. One part was used directly in cAMP assay and the other was further purified using affinity chromatography for α-MSH (Bachem AG) coated on activated UltraLink beads (Pierce, Rockford, Ill., USA). The α-MSH IgGdepleted IgG effluents were saved, lyophilized and diluted in PBS.

Affinity Kinetics Assay

Affinity kinetics of mouse IgG for ClpB and α-MSH was determined by a biospecific interaction analysis based on the surface plasmon resonance phenomenon on a BIAcore 1000 instrument (GE Healthcare). α-MSH (Bachem AG) or ClpB protein (Delphi Genetics) were diluted to 0.5 mg·ml$^{-1}$ in 10 mM sodium acetate buffer, pH 5.0 (GE Healthcare), and were covalently coupled on the sensor chips CM5 (GE Healthcare) by using the amine coupling kit (GE Healthcare). All measures were performed on the same α-MSH or ClpB-coated chips. For the affinity kinetic analysis, a multicycle method was run with five serial dilutions of each IgG sample: 3360, 1680, 840, 420 and 210 (nmol), including a duplicate of 840 nmol and a blank sample (HBS-EP buffer only). Each cycle included 2 min of analyte injection and 5 min of dissociation with flow speed 30 µl.min$^{-1}$ at 25° C. Between injections of each sample, the binding surface was regenerated with 10 mM NaOH, resulting in the same baseline level of the sensorgram. The affinity kinetic data were analyzed using BiaEvaluation 4.1.1 program (GE Healthcare). For fitting kinetic data, the Langmuir's 1:1 model was used, and the sample values were corrected by subtracting the blank values.

In Vitro cAMP Assay

Stable cell line of human embryonic kidney-293 cells expressing human MC4R was generated using a lentiviral transduction technology and purchased from Amsbio (Oxon, UK). High expression of MC4R mRNA in transfected cells was validated by reverse transcription PCR in Amsbio and in our laboratory. The presence of the transgene in cells before each experiment was verified by the visualization at a fluorescence microscope of the green fluorescent protein, which gene was inserted in the same with MC4R lentivector but under a different promoter. The α-MSH peptide (Bachem AG) was diluted in the induction buffer: PBS, 500 µM IBMX, 100 µM RO 20-1724 (Sigma), 20 mM MgCl2 to the final concentrations of 2, 1, 750, 500, 250, 100, 75, 50 and 10 nM corresponding to the α-MSH doses of 0.6, 3, 4.5, 6, 15, 30, 45, 60 and 120 µmol, respectively, and also included one blank sample. After unfreezing, the cells were cultured in 250 ml tissue culture flasks (BD-Falcon, Beckton-Dickinson, Bedford, Mass., USA) in Dulbecco's modified Eagle medium 4.5 g·l$^{-1}$ glucose (Eurobio, Courtaboeuf, France) supplemented with (2 mM L-glutamine, 10% fetal calf serum, 0.1 mM nonessential amino acids and 1% penicillin-streptavidin) in humidified cell culture incubator at 37° C., 5% CO2 for 8-10 days. At the day of experiment, cultured MC4R human embryonic kidney-293 cells were treated with 0.25% trypsin-EDTA (Sigma-Aldrich) and cell pellets were resuspended in PBS to obtain 5000 cells per well (10 µl) in a nontreated bioluminescence white 96-microwell plate (Nunc, Roskilde, Denmark). The cAMP production was measured using the bioluminescent assay cAMP-Glo Max Assay kit (Promega, Madison, Wis., USA) according to the manufacturer's instructions. In brief, the cells were incubated for 15 min at room temperature with different concentrations of α-MSH peptide alone or α-MSH together with mouse IgG pools from ClpB-immunized or adjuvant control groups, and which were added to the cells just before α-MSH. Serial dilutions of cAMP standard (provided by the kit) were assayed on the same microplate. cAMP detection solution was added to each well, then the cells were homogenized by agitation and centrifuged 2 min at 1000 r.p.m. and then incubated for 20 min at 23° C. Kinase-Glo reagent substrate was added in each well and after 10 min of incubation at 23° C., the luminescence was read with a bioluminescence instrument (Safas Spectrometer, Monaco). Three tests for each dilution were performed in separate wells and were repeated at two separate days resulting in n=6 for each point of the cAMP activation curve when native IgG were used. After depletion of native IgG from anti-α-MSH IgG fraction, the same experiment was performed with each α-MSH concentration and IgG as described above.

E. coli Gavage in Mice

One-month-old male C57Bl6 mice (Janvier Laboratories) were acclimated to the animal facility for 1 week and maintained as described above. Mice were distributed into four groups (n=8 in each) as follows: (i) gavaged with 108 E. coli K12 bacteria; (ii) gavaged with 108 E. coli K12 bacteria deficient for ClpB; (iii) gavaged with LB medium only; and (iv) controls that did not receive any treatments. The ClpB mutant strain was generated in the Bernd Bukau's Laboratory (ZMBH, Heidelberg University, Heidelberg, Germany) and was kindly provided together with the corresponding wildtype (WT) E. coli bacteria by Dr Axel Mogk. Mice were placed individually into the BioDAQ cages (Research Diets) and intragastrically gavaged daily before the onset of dark phase for 21 days with 0.5 ml of LB medium with or without bacteria. During the last day of gavage, mice feces were collected and frozen. After gavage, mice were killed by decapitation and trunk blood was collected into EDTA-containing tubes. Plasma was separated by centrifugation at 3500 r.p.m. (1.4 g) for 10 min at 4° C. and stored at −80° C. before assay. Plasma levels of anti-ClpB and anti-α-MSH IgG and IgM were assayed as described above.

ClpB DNA Assay

DNA was extracted from the cultures of the WT and ClpB mutant strains, and was also purified from mice feces using the QIAampR DNA Stool Mini Kit (Qiagen, France). Bacteria were dissolved in water and boiled at 100° C. during 5 min, after 1 min of centrifugation at 11 000 r.p.m., the supernatant containing the DNA was stored at −20° C. Using the NCBI primer design tool (http://www.ncbi.nlm.nih.gov/tools/primer-blast/), we designed the following nucleotide primers that amplify 180-base pair DNA region coding for the ClpB protein fragment containing one identified α-MSH-like epitope (FIG. 1e), forward: 5'-GCAGCTCGAAGGCAAAACTA-3' (SEQ ID NO: 4) and reverse: 5'-ACCGCTTCGTTCTGACCAAT-3' (SED ID NO: 5) (Invitrogen Custom Primers, Cergy Pontoise, France). PCR was performed in a thermocycler with Micro-Amp tubes (Eppendorf, Hambourg, Germany). The reaction was carried out in a 50-μl volume containing 25 μl of Go Taq Green Master Mix 2× (Promega), 1 μl (20 μmol) of each primer, 21 μl of bi-distilled water and 1 μl of bacterial DNA. PCR conditions were as follows: 3 min at 94° C. followed by 35 cycles at 94° C. for 30 s, 60° C. for 30 s and 72° C. for 1.5 min. PCR products were visualized on a 1% agarose gel (Sigma), with the expected size of 180 base pair and the specificity validated using ClpB mutant strain.

Plasma Concentrations of Bacterial ClpB Protein

Plasma concentrations of bacterial ClpB were measured using enzyme-linked immunosorbent assay (ELISA) according to the following protocol. Rabbit polyclonal anti-ClpB IgG, customly generated by Delphi Genetics (Gosselies, Belgium), were coated on to 96-well Maxisorp plates (Nunc, Rochester, N.Y.) using 100 μl and a concentration of 2 μg/ml in 100 mM NaHCO3 buffer, pH 9.6 for 24 h at 4° C. Plates were washed (5 min×3) in phosphate-buffered saline (PBS) with 0.05% Tween 200, pH 7.4. The recombinant ClpB protein, customly generated by Delphi Genetics, as a standard, was serially diluted to 5, 10, 25, 50, 70, 100 and 150 μM in the sample buffer (PBS, sodium azide 0.02%, pH 7.4) and added to the wells in duplicates. The plasma samples from patients with eating disorders and healthy controls (1:25 in sample buffer) were added to the remaining wells in duplicates and the ClpB standards and plasma samples were incubated 2 h at room temperature (RT). Plates were washed (5 min×3) in PBS with 0.05% Tween 200, pH 7.4. Mouse monoclonal anti-ClpB IgG (1:500 in sample buffer), customly generated by Delphi Genetics and pre-screened for having no cross-reactivity with α-MSH, were added to the wells and incubated 90 min at room temperature. Plates were washed (5 min×3) in PBS with 0.05% Tween 200, pH 7.4. Goat anti-mouse IgG conjugated with alkaline phosphatase (1:2000 in sample buffer) from Jackson ImmunoResearch Laboratories, Inc. (West Grove, Pa.) were added to the wells and incubated for 90 min at RT. Plates were washed (5 min×3) in PBS with 0.05% Tween 200, pH 7.4 and then 100 μl of p-nitrophenyl phosphate solution (Sigma, St. Louis, Mo.) was added as alkaline phosphatase substrate. After 40 min of incubation at room temperature, the reaction was stopped by adding 3N NaOH. The optical density (OD) was determined at 405 nm using a microplate reader Metertech 960 (Metertech Inc., Taipei, Taiwan). Blank OD values resulting from the reading of plates without addition of plasma samples or ClpB protein standard dilutions were subtracted from the sample OD values. Plasma concentrations of ClpB was calculated based on the OD of the ClpB standard curve and was adjusted for the plasma dilution.

Statistical Analysis

Data were analyzed and the graphs were plotted using the GraphPad Prism 5.02 (GraphPad Software Inc., San Diego, Calif., USA). Normality was evaluated by the Kolmogorov-Smirnov test. Group differences were analyzed by the analysis of variance or the nonparametric Kruskal-Wallis test with the Tukey's or Dunn's post tests, respectively, according to the normality results. Body weight changes were analyzed with two-way repeated measurements analysis of variance and the Bonferroni post tests. Individual groups were compared using the Student's t-test or the Mann-Whitney test according to the normality results. Effects of absorptions of ClpB antibodies with α-MSH were analyzed using paired t-test. Pearson's or Spearman's correlation coefficients were calculated according to the normality of the variable. The cAMP production was analyzed using a nonlinear regression fit (log(α-MSH) vs normalized cAMP response), which equation was $Y=100/(1+10(Log\ EC50-X)\times HillSlope)$. Data are shown as mean±s.e.m., and for all test, P<0.05 was considered statistically significant.

Results

Proteomic Identification of Bacterial α-MSH Mimetics

To identify bacterial proteins with molecular mimicry to α-MSH, a research strategy based on proteomic technology was developed. Total protein was extracted from E. coli K12 cultures, the cytoplasmic fraction was resolved by 2D gel electrophoresis (FIG. 1a) and transferred to a polyvinylidene difluoride membrane. To increase the probability of detection of multiple α-MSH-like epitopes in bacterial proteins, the membrane was revealed with polyclonal anti-α-MSH IgG. 13 immunopositive protein spots were found (FIG. 1b), among which the spots 1-8 disappeared after preadsorption of antibodies with $10^{-6}M$ α-MSH (FIG. 1c), confirming specific α-MSH-mimetic epitopes. Using mass spectrometry, protein spots 1, 2, 3 and 4, displaying the strongest α-MSH-like staining, were identified as isoforms of the heat-shock protein named ClpB, a 857-a.a. protein, 857 amino acid protein disaggregation chaperone or ClpB, MW 95526 (molecular weight: 95526 Da, accession number: NP_417083.1, SEQ ID NO: 1). Less intensely stained α-MSH-like spots 5-8 (with the highest MASCOT scores of 880, 877, 874 and 800, respectively) were isoforms of the 548-a.a. protein chaperonin GroEL, (molecular weight: 57293 Da; accession number: YP_001732912.1). An alternative strategy of E. coli protein separation was also used, using an OFFGEL fractionator followed by one-dimensional gel electrophoresis and western blot with anti-α-MSH IgG preadsorbed or not with α-MSH (data not shown). One band was specifically recognized by anti-α-MSH IgG and was found to contain the ClpB protein (with the highest MASCOT score of 1065). Based on these results, ClpB was selected as a target protein for further validation of its molecular mimicry with α-MSH. To analyze the amino-acid sequence homology between α-MSH and bacterial ClpB, both sequences were aligned in the Emboss Stretcher program that uses the Needleman-Wunsch algorithm (http://www.ebi.ac.uk/Tools/emboss/). The alignments revealed a site of the ClpB protein displaying discontinuous 5 a.a. sequence homology with α-MSH (FIG. 1d). This putative α-MSH-like epitope was located in an inter-helical loop of the ClpB protein structure indicating that it is exposed on the protein surface, that is, accessible to auto-Abs binding. Western blot of the recombinant ClpB protein revealed with anti-α-MSH IgG showed a 96-kDa band (FIG. 1e), confirming that the ClpB protein contains α-MSH-like epitope(s). These results show that the presence of at least five consecutive amino-acid sequence homology, according to the molecular mimicry concept is not an obligatory condition for bacterial proteins to be recognized by IgG crossreacting with a neuropeptide.

Immunization of Mice with ClpB

Figure 2B:
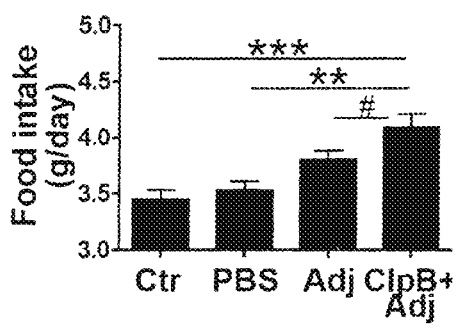
Figure 2C:
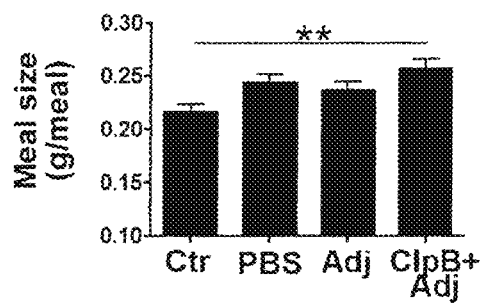
Figure 2D:
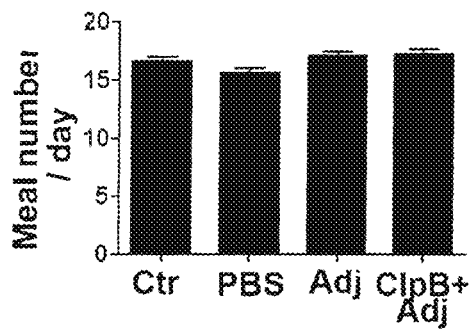
Figure 2E:
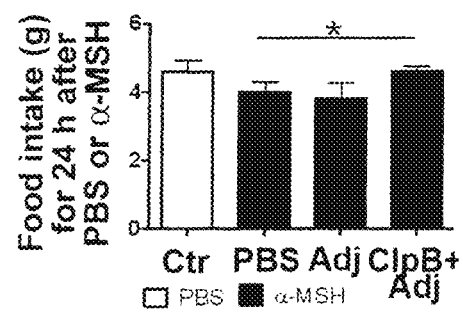
Figure 2F:
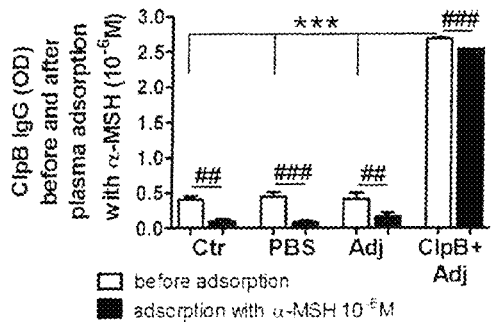
Figure 2G:
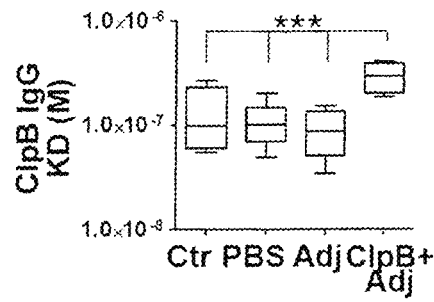
Figure 2H:
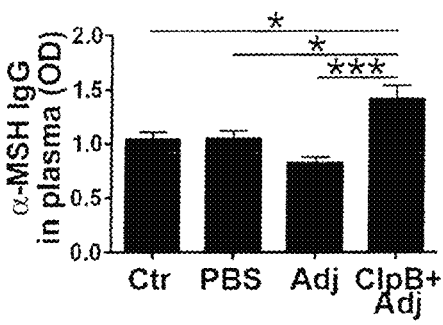
Figure 2I:
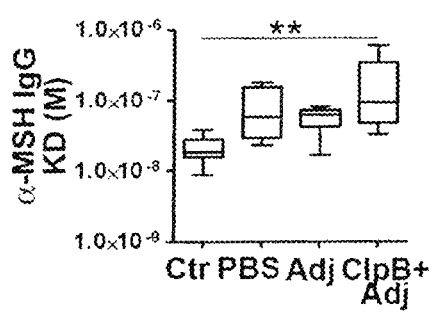

To investigate whether E. coli ClpB may induce auto-Abs crossreactive with α-MSH, influencing feeding and anxiety, mice were immunized with the recombinant bacterial ClpB protein. Mice that received ClpB together with adjuvant or adjuvant alone displayed lower body weight for a few days after injections (FIG. 2a). However, 4 weeks later, ClpB-immunized mice had higher body weight (+5%) vs controls (FIG. 2a). The mean daily food intake, as measured during the last 10 days of the experiment, was also higher (+13%) in ClpB-immunized mice as compared with other groups (FIG. 2b). The increase in food intake was owing to increased meal size (FIG. 2c), as meal number did not change (FIG. 2d), indicating that the ClpB immunization interfered with satiation rather than with hunger mechanisms. This is in agreement with the known role of α-MSH to induce satiation. To further validate the relevance of ClpB immunization to α-MSH anorexigenic effect, mice received i.p. injection of α-MSH. The following 24 h food intake and body weight were not affected in ClpB-immunized mice (FIG. 2e), indicating that they were not sensitive to the anorexigenic effect of administered α-MSH that was present in nonimmunized mice. After the feeding experiments, locomotor activity and anxiety related behavior in mice were studied in the open field and O-maze tests. The total locomotor activity and the time spent in the open vs border areas did not significantly differ between the study groups (data not shown). However, in the closed arms of the O-maze, the ClpB-immunized mice moved a shorter distance as compared with controls (data not shown) and spent less time as compared with all other groups (data not shown), indicating decreased anxiety. To confirm the efficiency of immunization, plasma levels of anti-ClpB IgG were assayed and their affinity measured. In ClpB immunized mice, a strong increase in anti-ClpB IgG levels (FIG. 2f) with lower affinities (FIG. 2g) were found, in agreement with recent IgG induction. Increased plasma levels of α-MSH-reactive IgG were also found in ClpB-immunized mice (FIG. 2h); these IgG were similarly characterized by lower affinities for α-MSH, as compared with controls (FIG. 2i). Adsorption of mouse plasma with α-MSH, significantly reduced plasma levels of anti-ClpB IgG, confirming that a fraction, but not all of the anti-ClpB IgG, were crossreactive with α-MSH (FIG. 2f). Plasma levels of α-MSH IgM auto-Abs did not significantly differ between the groups (data not shown). Whether ClpB immunization may induce auto-Abs crossreacting with the adrenocorticotropic hormone, a 39-a.a. peptide containing the α-MSH sequence was also analyzed. No significant differences in plasma adrenocorticotropic hormone-reactive IgG were found (data not shown), showing the selectivity of the conformational mimicry between ClpB and α-MSH.

Mouse IgG Effects on MC4R Signaling

Figure 2J:
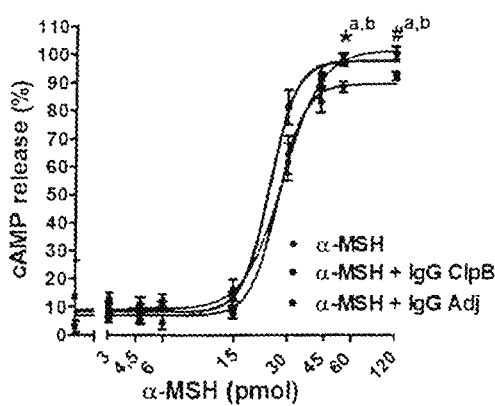
Figure 2K:
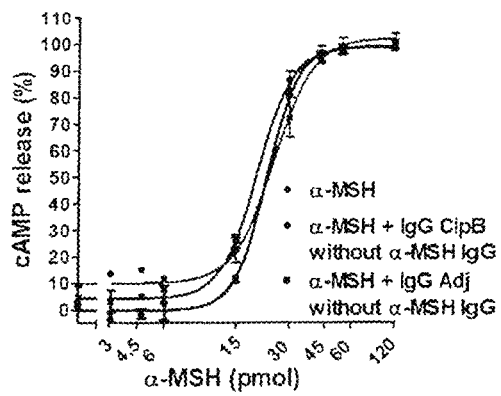

To determine the impact of ClpB immunization-induced α-MSH crossreactive IgG on MC4R signaling, their effects on α-MSH-induced cAMP production in MC4R-expressing cells were studied. cAMP concentrations were found to be lower when α-MSH was preincubated with IgG from ClpB-immunized mice, as compared with α-MSH alone or α-MSH preincubated with IgG from adjuvant injected mice, with a reduction of 8-10% at the two highest α-MSH concentrations (FIG. 2j). After depletion of α-MSH-reactive IgG from the pooled IgG, the remaining IgG from the ClpB immunized mice did not show any effect on α-MSH-induced cAMP release (FIG. 2k), indicating that anti-α-MSH crossreactive IgG in ClpB-immunized mice were responsible for lowering cAMP production in response to α-MSH. The reduction in MC4R activation and signaling may, hence, account for the increased food intake and decreased anxiety observed in ClpB-immunized mice.

Intragastric Delivery of E. coli in Mice

Figure 3A:
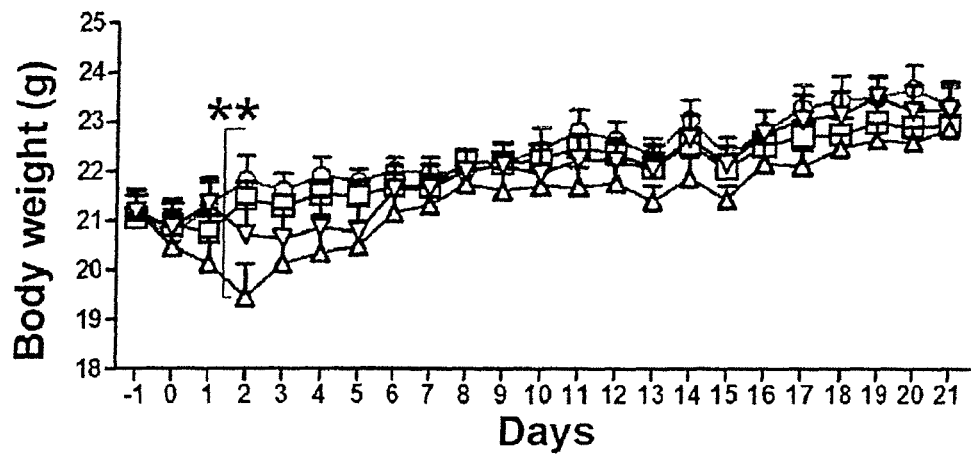
Figure 3B:
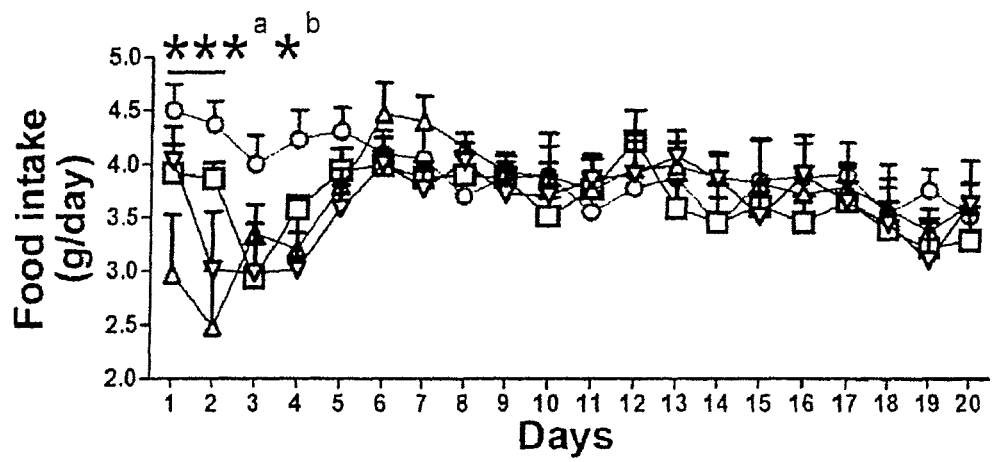
Figure 3C:
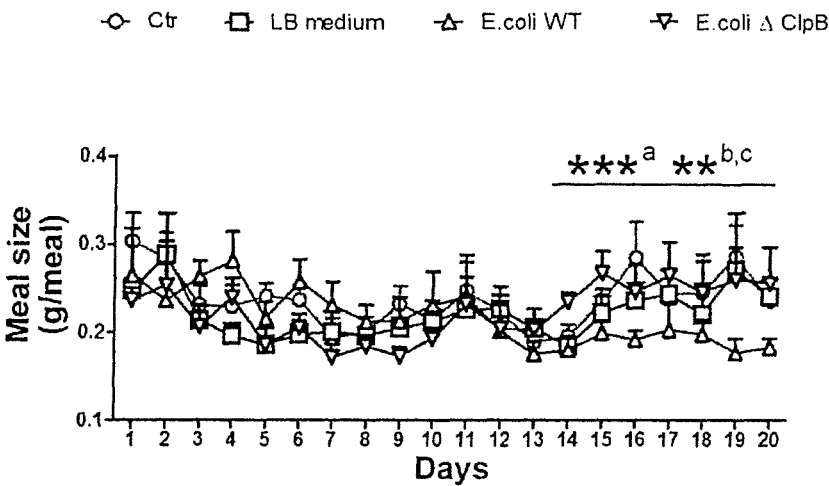
Figure 3D:
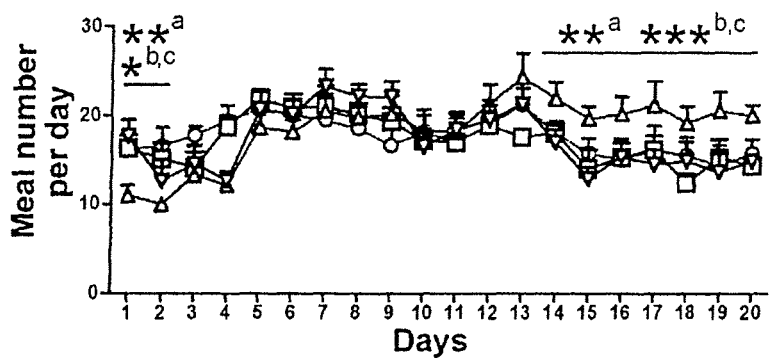
Figure 3E:
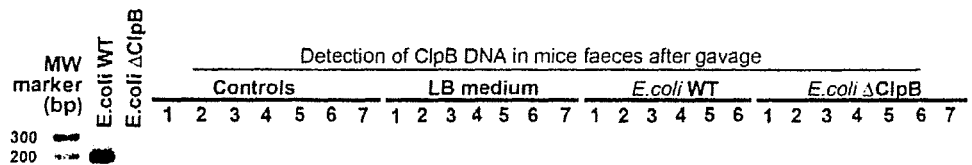
Figure 3F:
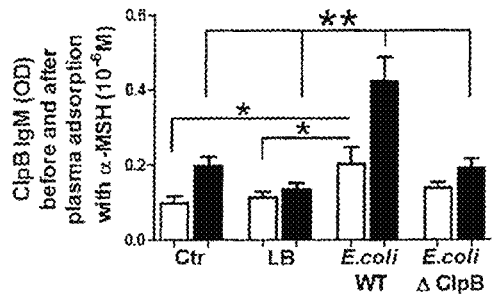
Figure 3G:
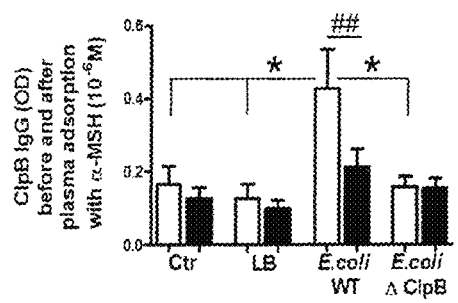
Figure 3H:
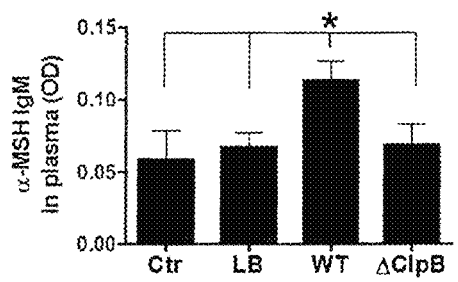
Figure 3I:
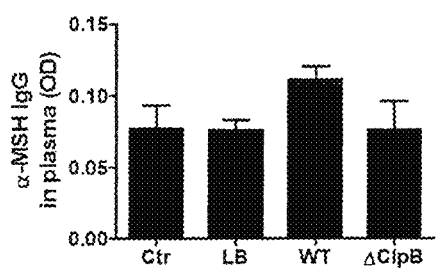
Figure 3J:
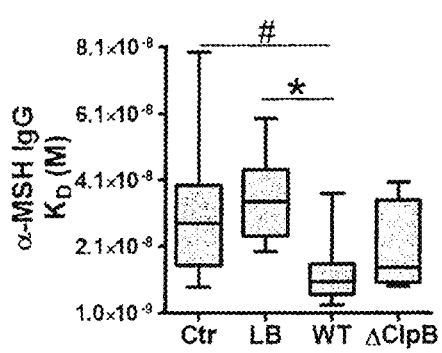

To test whether E. coli may induce immunogenic response against the ClpB protein, resulting in production of anti-ClpB auto-Abs crossreactive with α-MSH, WT and ΔClpB strains of E. coli K12 were given daily to mice by intragastric gavage during 3 weeks. Another group of mice was gavaged with the bacterial culture medium only, and the control group did not receive any treatment. The first days of gavage were accompanied by a decrease in body weight and food intake in mice receiving WT E. coli, which then gradually returned to control levels (FIGS. 3a and b). Again, during the last week of gavage, feeding pattern was affected in mice receiving E. coli WT showing a decrease in meal size but increase in meal number (FIGS. 3c and d). Remarkably, mice receiving ΔClpB E. coli did not significantly differ from controls in either body weight gain, food intake or feeding pattern at any time point. These data support specific involvement of bacterial ClpB in the host acute decrease of food intake as well as in the chronic regulation of feeding pattern following E. coli infection. Expectedly, ClpB DNA was more abundant in feces of mice receiving E. coli WT, although its low level was detected in some control mice (FIG. 3e). After 3 weeks of gavage, plasma levels of both anti-ClpB IgM and IgG were elevated in mice that received E. coli WT as compared with controls and ΔClpB E. coli groups (FIGS. 3f and g). Adsorption of plasma with α-MSH reduced anti-ClpB IgG levels in E. coli WT-gavaged mice (FIG. 3g), indicating the presence of anti-ClpB IgG crossreactive with α-MSH. Interestingly, plasma levels of the IgM class of anti-ClpB auto-Abs were increased after adsorption with α-MSH, suggesting that α-MSH caused dissociation of α-MSH IgM immune complexes crossreactive with ClpB that were increased in E. coli WT-gavaged mice (FIG. 3f). Plasma levels of anti-α-MSH IgM were also increased by E. coli WT delivery as compared with all other groups (FIG. 3h), while anti-α-MSHreactive IgG were only slightly increased without reaching significance (FIG. 3i). Nevertheless, affinity kinetic analysis of α-MSH IgG revealed lower values of the dissociation equilibrium constants in E. coli-gavaged mice (FIG. 3j), without significant changes of the association or dissociation rates (data not shown). These changes, including increased levels of the IgM class of α-MSH reactive auto-Abs, might reflect an immune response towards ClpB as to a novel antigen. In fact, low or undetectable levels of ClpB DNA in feces of mice that did not receive E. coli WT indicates that ClpB-expressing microorganisms were not major gut commensals in the studied mice. Thus, in contrast to ClpB-immunized mice, which showed increased levels of low-affinity anti-α-MSH IgG associated with increased meal size and body weight gain, E. coli-gavaged mice showed increased production of both anti-α-MSH-reactive IgM and IgG with increased affinities associated with decreased meal size and body weight.

Anti-ClpB Antibodies in ED Patients

Figure 4A:
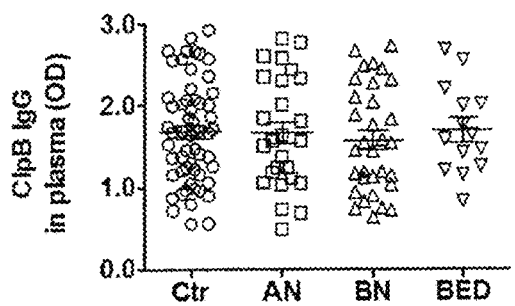
Figure 4B:
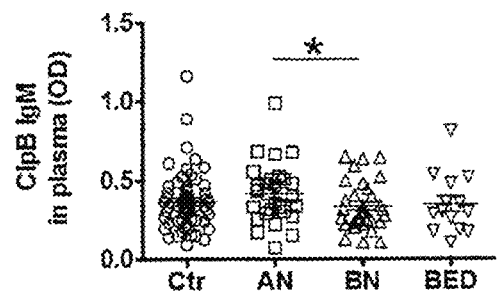
Figure 4C:
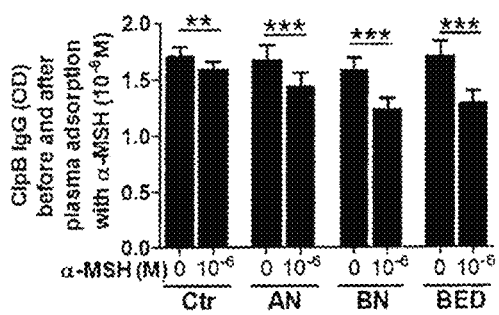
Figure 4D:
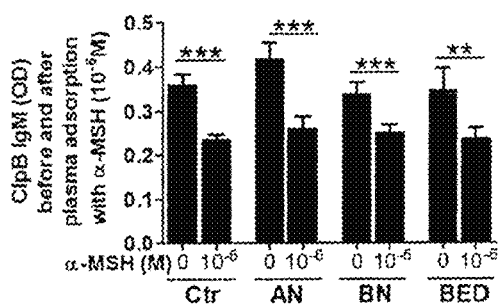
Figure 4E:
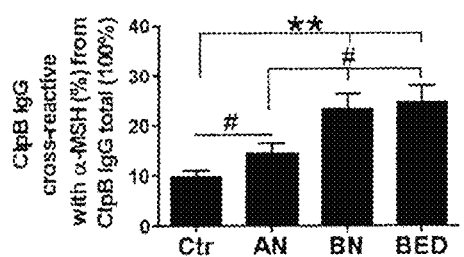
Figure 4F:
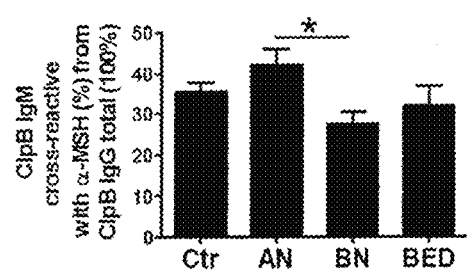

As the ability of the E. coli ClpB protein to stimulate production of α-MSH crossreactive auto-Abs was validated, the relevance of bacterial ClpB to ED was next determined by studying anti-ClpB antibodies in patients with AN, BN or BED. It was found that both anti-ClpB IgG and IgM were readily detectable in plasma of ED patients as well as healthy subjects with no significant differences of their mean levels (FIGS. 4a and b). However, there was high variability in all study groups, indicating a different individual history in encountering ClpB-like antigens. To verify whether human anti-ClpB antibodies similarly were crossreactive with α-MSH, plasma samples were adsorbed with $10^{-6}$M α-MSH, leading to significant reduction of anti-ClpB IgG and IgM detectable levels in all study groups (FIGS. 4c and d). Further, the relative levels of α-MSH crossreactive anti-ClpB IgG were increased in all three groups of ED patients, in particular BN and BED vs healthy controls (FIG. 4e). Elevated levels of α-MSH crossreactive anti-ClpB IgM were found in AN as compared with BN (FIG. 4f). To further determine the relevance of anti-ClpB IgG and IgM to ED, it was studied whether their plasma levels may correlate with behavioral traits in ED patients and controls measured by the EDI-2. It was found that in controls, ClpB IgG correlated inversely with the normal range of a few psychological traits, but in AN patients, ClpB IgG levels correlated positively with the core psychopathological traits such as body dissatisfaction and drive for thinness (Table 1). Moreover, in AN and BED patients, EDI-2 subscale scores correlated with ClpB IgM in the opposite way, being negative in AN but positive in BED (Table 1). However, in BED patients, ClpB IgM correlated negatively with age, suggesting that the highest anti-ClpB IgM levels were associated with the acute form of the disease. Remarkably, the correlations found in AN patients between ClpB IgG or IgM and drive for thinness or interpersonal distrust, respectively, resembled closely the correlations between the same psychological traits and α-MSH-reactive IgG or IgM found in a different group of AN patients in a previous study.

hence, that ClpB-expressing microorganisms as a novel specific target for diagnostics and treatment of ED.

Example 2

This example demonstrates the effect of ClpB-expressing bacteria on obese ob/ob mice.

Genetically obese ob/ob mice were acclimated to the animal facility for 1 week and maintained as described above. Mice were intragastrically gavaged with (i) $10^8$ E. coli K12 bacteria (expressing ClpB); (ii) $10^8$ E. coli K12 bacteria deficient for ClpB; both in Mueller-Hilton (MH) medium or with (iii) MH medium only, as a control. The ClpB mutant strain was generated in the Bernd Bukau's Laboratory (ZMBH, Heidelberg University, Heidelberg, Germany) and was kindly provided together with the corresponding wildtype (WT) E. coli bacteria by Dr. Axel Mogk. Mice were placed individually into the BioDAQ cages (Research Diets) and intragastrically gavaged daily for 21 days as indicated.

TABLE 1

Significant correlations between plasma levels of anti-ClpB IgG and IgM and psychological traits in eating disorder patients and controls (Contr.) assayed by the Eating Disorder Inventory-2.

| ClpB IgG (Contr.) | Maturity fears $r = -0.31$ * | Impulse regulation $r = -0.26$ * | Social insecurity $r = -0.26$ * | |
|---|---|---|---|---|
| ClpB IgG (AN) | Body dissatisfaction $r = 0.4$ * | Drive for thinness $r = 0.35$ * | Perfectionism $r = 0.38$ * | |
| ClpB IqM (AN) | Ineffectiveness $r = -0.42$ * | Interpersonal distrust $r = -0.58$ ** | Social insecurity $r = -0.52$ ** | Anhedonia $r = -0.35$ * |
| ClpB IgM (BED) | Bulimia $r = 0.53$ * | Perfectionism $r = 0.6$ * | Age $r = -0.74$ ** | |

All Spearman's r * p < 0.05, ** p < 0.01, except Pearson's r * p < 0.05 for perfectionism. (n = 65 Contr., n = 27 AN, and n = 14 BED).

Plasma Concentrations of Bacterial ClpB Protein

ClpB protein was detected in plasma samples of all study subjects ranging from 10 μM to 180 μM with a mean level of about 30 μM in healthy controls. Mean plasma levels of ClpB were significantly elevated in all groups of patients with eating disorders, including AN, BN and BED (see FIG. 5). By applying the common criteria of a diagnostically-relevant changes of concentrations equal or exceeding 2 standard deviations, 21.7% of AN, 32% of BN and 25% of BED patients showed increased levels of plasma ClpB.

Conclusion

The results reveal a molecular link between ClpB expressing gut bacteria and the regulation of motivated behavior and emotion via production of ClpB protein and anti-ClpB antibodies crossreactive with α-MSH. It shows that specific alterations of gut microbiota may lead to behavioral and emotional abnormalities as observed in ED patients. The findings of increased levels of ClpB protein and anti-ClpB IgG crossreactive with α-MSH in ED patients and correlations of anti-ClpB antibodies with patient's psychopathological traits support the involvement of ClpB-expressing microorganisms in increased ClpB antibody production and establishment of abnormal feeding behavior and emotion. In conclusion, the results identify ClpB as a protein responsible for the origin of auto-Abs crossreactive with α-MSH, associated with psychopathological traits in ED patients and, The inventors showed that gavage with E. coli K12 WT bacteria induced a 56% reduction in weight gain (FIGS. 6 and 7), a reduced fat mass/lean mass ratio (FIGS. 8 and 9) and a reduction of 20% of the total food intake (FIGS. 10 and 11), which was not observed with E. coli K12 bacteria deficient for ClpB.

Example 3

This example demonstrates the effect of other strains of bacteria expressing ClpB on obese ob/ob mice.

Genetically obese ob/ob mice were acclimated to the animal facility for 1 week and maintained as described above. Mice were intragastrically gavaged with (i) $10^8$ E. coli K12 bacteria (expressing ClpB); (ii) $10^8$ E. coli Niessle 1917 bacteria (expressing ClpB) (iii) $10^8$ E. coli Niessle 1917 bacteria (expressing ClpB) in lyophilized form; all in Mueller-Hilton (MH) medium or with (iv) MH medium only, as a control. Mice were intragastrically gavaged daily for 14 days as indicated.

The inventors showed that gavage with any strain of E. coli ClpB-expressing bacteria induced a reduction in weight gain (FIGS. 12 and 13) and a reduction in fat content (FIG. 14).

Example 4

This example demonstrates the effect of ClpB-expressing *Hafnia alvei* on obese ob/ob mice.

Genetically obese ob/ob mice were acclimated to the animal facility for 1 week and maintained as described above. Mice were intragastrically gavaged with (i) $10^8$ *Hafnia alvei* AF036 bacteria (expressing ClpB); (ii) $10^8$ *E. coli* K12 bacteria deficient for ClpB; (iii) $10^8$ *E. coli* Niessle 1917 bacteria (expressing ClpB); all in Mueller-Hilton (MH) medium or with (iv) MH medium only, as a control.

The inventors show that treatment with *Hafnia alvei* induced a significant decrease in body weight gain as compared to obese controls (FIG. 15). Moreover, the decrease in body weight gain was associated with a decrease of cumulative food intake (FIG. 16), and with a decrease of both fat and lean masses, without alteration of the lean/fat mass ratio (FIG. 17).

Example 5

This example demonstrates the effect of ClpB-expressing *Hafnia alvei* on high fat diet-induced obese mice.

One-month-old male C57Bl6 mice (Janvier Laboratories) were induced with high fat/high carbs diet for 2 weeks. Mice were then intragastrically gavaged with (i) $10^8$ *Hafnia alvei* AF036 bacteria (expressing ClpB); (ii) $10^8$ *E. coli* K12 bacteria deficient for ClpB; both in Mueller-Hilton (MH) medium or with (iii) MH medium only, as a control. Mice were placed individually into the BioDAQ cages (Research Diets) and intragastrically gavaged daily for 21 days as indicated.

Induction of obesity by high fat diet was validated by measurement of mean body weight (FIG. 18A), fat mass (FIG. 18B) and lean mass (FIG. 18C) in a group induced and a group non-induced for obesity.

The inventors showed that gavage with any strain of *Hafnia alvei* ClpB-expressing bacteria induced a reduction in weight gain (FIG. 19) and a reduction in fat content (FIG. 20).

Example 6

Hormone-sensitive lipase (HSL) is an intracellular neutral lipase that is capable of hydrolyzing triacylglycerols, diacylglycerols, monoacylglycerols, and cholesteryl esters, as well as other lipid and water-soluble substrates. In particular, activation of HSL induces lipolysis. Hormonal activation of HSL occurs via cyclic AMP dependent protein kinase (PKA), which phosphorylates HSL. An increase of the expression of the phosphorylated form of HSL protein (pHSL) means thus activation of lipolysis. Expression of pHSL was measured by western blot.

To evaluate the possible effects of *H. alvei* HA4597 supplementation on fat tissue lipolysis, the levels of pHSL protein, a lipolytic marker, were studied by WB in the epididymal fat tissue of both models using anti-pHSL antibodies (Cell Signaling Technology, Mass., USA).

The inventors showed that gavage with *E. coli* Niessle 1917 and *Hafnia alvei* bacteria increased pHSL expression (FIG. 21) as compared to control and gavage with *E. coli* K12 bacteria. Therefore, *E. coli* Niessle 1917 and *Hafnia alvei* bacteria activate the mechanism of lipolysis.

Example 7

Previous data on leptin-deficient ob/ob obese mice show the effects of *H. alvei* on the food intake reduction with no impact on the fat mass/lean mass ratio. However, in the following High Fat Diet (HFD) model, the anti-obesity effects as well as the reduction of fat mass/lean mass ratio were confirmed. Therefore, the administration of *H. alvei* not only decreased food intake/body weight gain, but also improved body composition.

Experimental Conditions

Animal care and experimentation were done in accordance with guidelines established by the National Institutes of Health, French and European Community regulations (Official Journal of the European Community L 358, 18 Dec. 1986) and were approved by the Local Ethical Committee of Normandy (n° 5986). Six-to-seven-week-old male ob/ob mice (B6.V-Lep ob/ob JRj–n=88) were purchased from Janvier Labs (Le Genest-Saint-Isle, France), and, upon arrival, they were kept in a specialized air-conditioned animal facility (22±2° C., relative humidity 40±20%, reverse 10:00 p.m. to 10:00 a.m. light/dark cycle). During acclimation to the animal facility (from day (D)–19 to D–12), mice were housed in standard holding cages (n=3 per cage) with pelleted standard rodent chow (3430 standard diet, KlibaNafag, Kaiseraugst, Switzerland) and drinking water available ad libitum. After acclimation, the mice were weighed and placed in a restraint cylinder, and their body composition, including lean and fat mass, as well as body fluids, was measured, using the MiniSpec LF50 (Bruker, Rheinstetten, Germany). Then, according to body weight, the animals were randomly divided into two groups: (i) fed with a HFD (n=72, 45 kcal % fat, 35 kcal % carbohydrates, 20 kcal % proteins, energy density 4.7 kcal/g, D12451, Research Diets, New Brunswick, N.J., USA) and (ii) fed with a standard diet (SD; n=16, 5 kcal % fat, 75 kcal % carbohydrates, 20 kcal % proteins, energy density 3.8 kcal/g, 3430 KlibaNafag). The animals underwent a 5-day "induction" to both diets, followed by 1 week of daily handling protocol, where they were sham-treated (oral gavage of 200 μL of NaCl 0.9%, using rounded-end cannulas, Socorex, Ecublens, Switzerland) twice a day (approximatively 10:00 a.m. and 17:00 p.m.) from D–7 to D0 (FIG. 1). This procedure has been found to reduce stress-related effects on the body weight in chronic studies. During the baseline period and the later treatment sessions, body weight, as well as food intake (by cage), were measured daily, before the morning gavage (at approximatively 9:30 a.m.).

Toward the end of the baseline (D0), body composition was measured for a second time, using the MiniSpec LF50 (Bruker), and the HFD-fed animals were randomly divided into 3 subgroups (n=24 in each). All animals from the same cage were affiliated to the same subgroup. From D0 onward, animals from each of the 3 HFD-fed groups were treated daily for 38 days, at approximatively 7:00 p.m., by intragastric gavage, with a volume of 5 mL/kg containing either: (i) *H. alvei* HA4597™ provided by Biodis (Noyant, France) for TargEDys SA (1.4×1010 CFU/day in NaCl 0.9%); (ii) orlistat 80 mg/kg/day in NaCl 0.9% (Tocris BioScience, Bristol, UK); or (iii) NaCl 0.9% as a vehicle. The standard diet (SDiet)-fed controls received the same 5 mUkg volume of NaCl 0.9% by intragastric gavage (FIG. 22).

After five days of the DIO induction phase (Diet induced obesity), HFD-fed mice presented a significant increase of body weight as compared to SDiet-fed mice (44.7±0.4 g vs. 39.5±0.9 g at D–7, $p<0.001$), which persisted during the sham-treatment period of the DIO induction. The total daily food intake and the cumulative caloric intake were increased in HFD-fed vs. SDiet-fed mice during the sham-treatment period. At the end of the sham period, an increase of fat mass and percentage of body fat was found in HFD-fed mice. In spite of a small increase of the lean mass, its body percentage was lower in HFD-fed vs. SDiet-fed mice. The changes of body composition led to an overall decrease of lean/fat mass ratio in the HFD group. No significant changes of the body composition were observed in the SDiet group during sham treatment.

At D38, the body composition of all animals was measured, using the MiniSpec LF50, and treatment groups were divided into two sub-groups, for the oral glucose tolerance test (OGTT) after overnight fasting and for the baseline plasma glucose assay. An overnight fasting, after the removal of food during D22 light phase, (approximatively at 17:00 p.m.) was performed on half of each group, while food remained available ad libitum for the rest of the animals. The next morning, the mice received 30% glucose solution (2 g/kg) via intragastric gavage. Blood samples (one drop from tail tip) were taken every 15 min during 2 h, for glucose assay, using a glucometer (FreeStylePapillon Vision, Abbott Diabetes Care, Oxon, UK). Mice which didn't undergo the fasting procedure were anesthetized right after body composition measurements on D38 by intraperitoneal injection of ketamine/xylazine solution (80:10 mg/kg). Terminal blood samples (approximately 0.5 mL) were taken by a puncture of abdominal aorta in tubes coated with lithium heparin, which were stored at 4° C., until biochemical measurements of obesity-related metabolic markers using IDEXX Catalyst® One technology (Catalyst® Chem 17 CLIP+Catalyst® TRIG, IDEXX, Laboratories, Inc., Westbrook, Me., USA). Results, expressed as mean±standard error of means (SEM), were analyzed, using GraphPad Prism 5.02 (GraphPad Software Inc., San Diego, Calif., USA), with a p-value <0.05 considered as statistically significant. Longitudinal group differences were compared by the two-way repeated measurement (RM) analysis of variance (ANOVA) with Bonferroni's posttests. Individual differences were analyzed, using Student's t-test or Mann-Whitney's test according to normality evaluated by the D'Agostino-Pearson's test.

Confirmation of Effects on Body Weight

HFD-fed control mice displayed increased body weight gain as compared to SDiet-fed mice (FIG. 23A-C). Supplementation of *H. alvei* in HFD mice resulted in a decreased body weight gain vs. untreated HFD group, as compared by the area under curve (FIG. 3C), reaching a difference of 15.3% at the end of the treatment (FIG. 23B). Accordingly, the body weight gain of the *H. alvei*-treated group was 58.1% lower as compared to the difference between HFD and SDiet groups, although such decrease did not reach significance by ANOVA (FIG. 23B). The orlistat-treated group showed a significant decrease in body weight gain as compared to both the HFD control and *H. alvei* groups, reaching to the level of the SDiet-fed group (FIG. 23A-C).

Body Composition Effect

HFD increased percentage of fat mass and decreased percentage of lean mass, resulting in lower lean/fat mass ratio vs. SDiet-fed mice (FIG. 24A-C). *H. alvei* treatment alleviated the increase of adiposity and loss of lean mass associated with HFD (FIG. 24A,B). These changes led to a significant improvement of the lean/fat mass ratio in mice treated with *H. alvei* (FIG. 24C). Orlistat-treated HFD mice displayed similar improvements of body composition to the mice treated with *H. alvei* (FIG. 24A-C).

The reduction of the fat mass on lean mass ratio is further confirmed by the clinical data of example 9.

Food Intake and Weight-Loss without Induction of Hyperphagia

Daily food intake was higher in HFD controls vs. SDiet-fed mice during the first three weeks, and then it declined to the level of the SDiet group (FIG. 25A). *H. alvei* HA4597™-treated HFD-fed mice displayed similar daily food intake to SDiet-fed mice (FIG. 25A). Cumulative food intake was also reduced in *H. alvei* HA4597™-treated mice as compared to HFD controls (FIG. 25B,C). In the end of *H. alvei* HA4597™ treatment, at D38, the cumulative food intake was lower by 26.7 g vs. the HFD controls (FIG. 25C). Orlistat-treated mice displayed hyperphagia throughout the treatment (FIG. 25A), resulting in an increased cumulative food intake (FIG. 25B,C).

Example 8

In the experimental conditions of example 7 the following obesity-related parameters were assessed.

At D38, the body composition of all animals was measured, using the MiniSpec LF50, and treatment groups were divided into two sub-groups, for the oral glucose tolerance test (OGTT) after overnight fasting and for the baseline plasma glucose assay. An overnight fasting, after the removal of food during D22 light phase, (approximatively at 17:00 p.m.) was performed on half of each group, while food remained available ad libitum for the rest of the animals. The next morning, the mice received 30% glucose solution (2 g/kg) via intragastric gavage. Blood samples (one drop from tail tip) were taken every 15 min during 2 h, for glucose assay, using a glucometer (FreeStylePapillon Vision, Abbott Diabetes Care, Oxon, UK). Mice which didn't undergo the fasting procedure were anesthetized right after body composition measurements on D38 by intraperitoneal injection of ketamine/xylazine solution (80:10 mg/kg). Terminal blood samples (approximately 0.5 mL) were taken by a puncture of abdominal aorta in tubes coated with lithium heparin, which were stored at 4° C., until biochemical measurements of obesity-related metabolic markers using IDEXX Catalyst® One technology (Catalyst® Chem 17 CLIP+Catalyst® TRIG, IDEXX, Laboratories, Inc., Westbrook, Me., USA).

Effects on Glycaemia

Figure 26A:
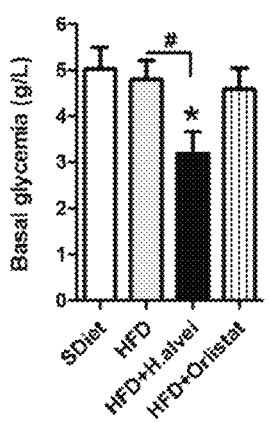
Figure 26B:
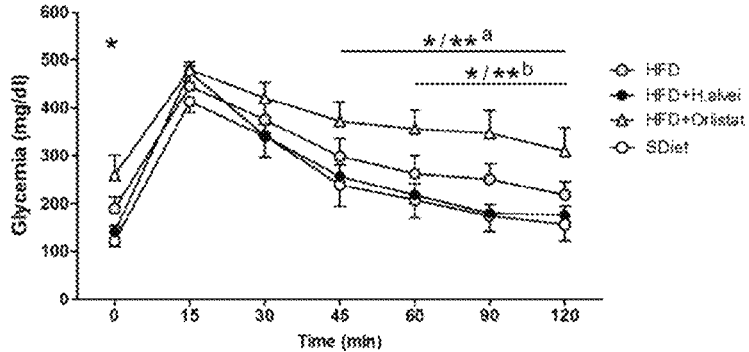

Ad libitum HFD-fed *H. alvei*-treated mice displayed a significant decrease, by about 1.5-fold, of the basal glucose plasma levels as compared to both the SDiet and HFD-fed controls (FIG. 26A). The OGTT test after an overnight fasting showed elevated levels of fasting glycemia in HFD-fed control mice (Student's t-test p<0.05) and in orlistat-treated mice as compared to SDiet-fed controls (FIG. 26B). After the oral glucose load, a 15 min peak of glucose was observed in all groups, without significant difference. A return to the baseline was delayed in the orlistat-treated mice as compared to both SDiet-fed and *H. alvei* HA4597™-treated mice (FIG. 26B).

Figure 26C:
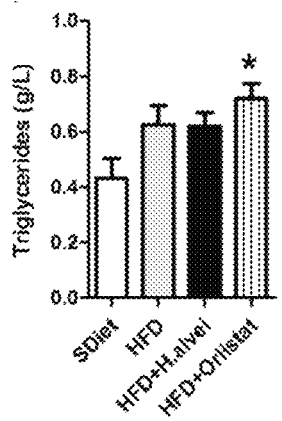
Figure 26D:
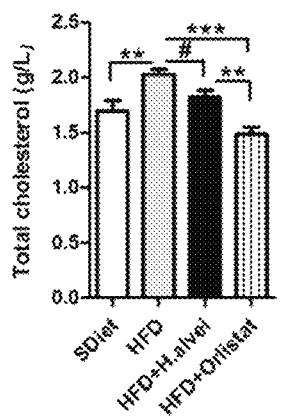
Figure 26E:
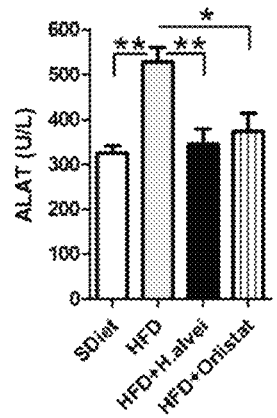

Effects on Lipidemic Parameters: Blood Lipids Cholesterol and Alanine Aminotransferase Triglycerides plasma level increased, although not significantly, in HDF-fed mice as compared to SDiet, and no significant effect of *H. alvei* on plasma triglycerides was observed (FIG. 26C). In HFD+Orlistat mice, triglycerides plasma level increased significantly (FIG. 26C). Total cholesterol plasma level increased significantly in HFD-mice as compared to control HFD-mice, and this increase was prevented in *H. alvei*-treated HFD-mice (FIG. 26D). Orlistat reduced total cholesterol even more than *H. alvei* (FIG. 26D). Plasma levels of alanine aminotransferase (ALAT), an indicator of obesity-induced steatohepatitis, were increased in HFD-mice as compared to SDiet-mice; treatment with either *H. alvei* HA4597™ or orlistat prevented this ALAT increase (FIG. 6E).

In contrast to the anorexigenic effect of *H. alvei*, orlistat, although efficient to reduce body weight in HFD-fed mice, induced a strong hyperphagic effect, which was most likely due to the decreased fat absorption in the gut. At the end of treatment period, food intake in the orlistat-treated HFD-mice was markedly increased, and, consequently, the difference between orlistat and H. alvei effects on the reduction of body weight gain tended to decrease. Moreover, such compensatory hyperphagia was accompanied at the end of the treatment period by increased basal and OGTT-induced plasma glucose levels. Although these orlistat-induced unwanted effects might be specific to this animal model, they suggest that H. alvei-induced moderate but sustained reduction of body mass gain through decreased food intake, along with beneficial metabolic effects, may represent a safer and more-efficient strategy for long-term body weight management. The present example shows that a daily provision of the H. alvei strain in genetically obese and hyperphagic ob/ob mice with HFD-exacerbated obesity decreased body weight gain, improved body composition, decreased food intake, and ameliorated several metabolic parameters, including plasma glucose and total cholesterol levels. These data further preclinically validate the anti-obesity efficacy of H. alvei as a potential new-generation nutraceutical or Life biotherapeutic for appetite and body weight control in obesity as well as preventing or treating diet-induced alterations of glucose and lipid metabolism.

Example 9

$10^{11}$ cells of *Hafnia alvei* HA4597™ per diem were orally administered in Double-blind, randomised, placebo-controlled Clinical Trial that lasted 12 weeks. The subjects (20-65 years old, mean age 46.4; 127 female subjects and 103 male subjects; mean BMI 27.84; mean waist circumference 101.3 cm; mean hip circumference 106.2 cm) were divided in a 2-arm trial There were statistically significant differences in the proportion of subjects who lost at least 3% of baseline body weight at 12 weeks between the study groups (V: 57.7% vs. P: 41.7%; pexF=0.028). The results were confirmed by the absolute body weight and BMI. Furthermore, there were statistically significant differences in the reduction in hip circumference from baseline to visit v4 (2 months) between the study groups at 8 weeks ($p_U$=0.002). The reduction in hip circumference was also significant from baseline to visit v5 (3 months) between the study groups at 12 weeks ($p_U$<0.001).

There were statistically significant differences in the feeling of fullness between the study groups at 12 weeks ($p_U$=0.009).

There clinical trial showed statistically significant differences in Glucose between the study groups at 12 weeks ($p_U$=0.027).

Lastly, in further endpoints of the study:
statistically significant changes in Cholesterol from visit v1 to visit v5 at week 12 ($p_{Wi}$=0.011) that were present in the H. alvei treated group and not in the placebo group,
statistically significant changes in LDL-cholesterol from visit v1 to visit v5 at week 12 ($p_{Wi}$=0.039) that were present in the H. alvei treated group and not in the placebo group.

The study further showed no statistically significant adverse effects as well as an overall good tolerability.

The above clinical data confirm the previous in vivo evidence, the oral administration of H. alvei having a significant effect on body weight, BMI, hip circumference reduction, fullness sensation induction. Such treatment further shows a positive impact on the metabolic parameters of glycemia, total cholesterol and LDL-cholesterol.

The invention claimed is:

1. A method of treating or attenuating obesity-related manifestations in a human or non-human mammal subject in need thereof, said method comprising orally administering to the subject a composition comprising an effective amount of *Hafnia alvei* probiotics; wherein said obesity-related manifestations are selected from the group consisting of hyperphagia, increased fat mass on lean mass ratio, increased waist circumference, postprandial hyperglycemia, fasting hyperglycemia and hypercholesterolemia; and
  wherein the subject is obese or overweight.

2. The method according to claim 1, wherein the subject has at least 180 or at least 200 mg/dL of total cholesterol and/or at least 100 or at least 130 mg/dL of LDL cholesterol.

3. The method according to claim 1, wherein the subject has at least 80 or at least 100 mg/dL of glucose at a fasting state.

4. The method according to claim 1, wherein the subject has at least 80 or at least 90 waist-to-hip ratio.

5. The method according to claim 1, wherein *Hafnia alvei* probiotics are administered at a dose between 1000 million and 10000 million UFC.day-1.

6. The method according to claim 1, wherein the *Hafnia alvei* probiotic is administered to the subject in the form of a pharmaceutical composition.

7. The method according to claim 1, wherein the *Hafnia alvei* probiotic is administered to the subject in the form of companion composition to be administered simultaneously or sequentially with a pharmaceutical composition in a method of treatment of a metabolic syndrome condition selected from the group consisting of hyperglycemia, hypercholesterolemia, and hepatic disfunction.

8. The method according to claim 1, wherein the *Hafnia alvei* probiotic is administered to the subject in the form of a nutraceutical or food complement composition.

* * * * *